(12) United States Patent
Ifuku et al.

(10) Patent No.: US 8,785,144 B2
(45) Date of Patent: Jul. 22, 2014

(54) ELECTRIC ANALYSIS METHOD

(75) Inventors: Yasuo Ifuku, Tokyo (JP); Nagamoto Murai, Tokyo (JP)

(73) Assignee: Mitsubishi Chemical Medience Corporation, Tokyo (JP)

( * ) Notice: Subject to any disclaimer, the term of this patent is extended or adjusted under 35 U.S.C. 154(b) by 596 days.

(21) Appl. No.: 12/922,971

(22) PCT Filed: Mar. 17, 2009

(86) PCT No.: PCT/JP2009/055170
§ 371 (c)(1),
(2), (4) Date: Sep. 16, 2010

(87) PCT Pub. No.: WO2009/116534
PCT Pub. Date: Sep. 24, 2009

(65) Prior Publication Data
US 2011/0014633 A1    Jan. 20, 2011

(30) Foreign Application Priority Data
Mar. 17, 2008    (JP) ................................ 2008-068257

(51) Int. Cl.
*G01N 33/53*    (2006.01)
(52) U.S. Cl.
USPC ................. 435/7.91; 435/285.2; 435/173.1; 435/173.2; 435/7.9
(58) Field of Classification Search
USPC ............. 435/285.2, 173.1, 173.2, 287.2, 7.9, 435/7.91
See application file for complete search history.

(56) References Cited

U.S. PATENT DOCUMENTS

| | | | | |
|---|---|---|---|---|
| 5,842,983 | A * | 12/1998 | Abel et al. | 204/403.1 |
| 2002/0055127 | A1 * | 5/2002 | Gindilis | 435/7.9 |
| 2005/0112544 | A1 * | 5/2005 | Xu et al. | 435/4 |
| 2007/0039835 | A1 * | 2/2007 | Rossier et al. | 205/792 |
| 2009/0098662 | A1 | 4/2009 | Birch et al. | |
| 2009/0310743 | A1 * | 12/2009 | Carpenter et al. | 378/45 |

FOREIGN PATENT DOCUMENTS

| | | |
|---|---|---|
| CN | 1985172 A | 6/2007 |
| JP | 04-080651 A | 3/1992 |
| JP | 10-260156 A | 9/1998 |
| JP | 2000-097899 A | 4/2000 |
| JP | 2001-153838 A | 6/2001 |
| JP | 2004-219325 A | 8/2004 |
| JP | 2004-257996 A | 9/2004 |

(Continued)

OTHER PUBLICATIONS

Hwang, S. et al., "Electrochemical Detection of DNA Hybridization Using Biometallization," *Analytical Chemistry*, Jan. 15, 2005, vol. 77, No. 2, pp. 579-584.

(Continued)

*Primary Examiner* — Melanie Y Brown
(74) *Attorney, Agent, or Firm* — Kilpatrick Townsend & Stockton LLP

(57) ABSTRACT

Disclosed is an analysis method comprising the steps of:
(a) reacting a substance to be analyzed with at least a specific partner which exhibits a selective interaction with the substance, converting a soluble substance to an insoluble substance by an insolubilization reaction, in correlation with the amount of the substance to be analyzed contained in a sample, and depositing the insoluble substance on a sensing part, and
(b) electrically analyzing the insoluble substance deposited on the sensing part,
wherein at least one of steps (a) and (b) is carried out under flow conditions.

14 Claims, 21 Drawing Sheets

(56) References Cited

FOREIGN PATENT DOCUMENTS

| | | |
|---|---|---|
| JP | 2005-024483 A | 1/2005 |
| JP | 2007-263914 A | 10/2007 |
| WO | 2005/121792 A1 | 12/2005 |

OTHER PUBLICATIONS

International Search Report mailed on Jun. 23, 2009, for International Application No. PCT/JP2009/055170 filed on Mar. 17, 2009, 4 ages, with English translation.

\* cited by examiner

ELECTRIC ANALYSIS METHOD

TECHNICAL FIELD

The present invention relates to an electric analysis method. The term "analysis" as used herein includes a detection to judge the presence or absence of a substance to be analyzed, and a measurement to quantitatively or semi-quantitatively determine the amount of the substance to be analyzed.

BACKGROUND ART

In analyses of biological samples such as clinical tests, an analysis method with a high detection sensitivity and accuracy is desired, because in many cases a trace amount of a compound has to be measured. As such an analysis method, not only a method utilizing a specific interaction, such as an antigen-antibody reaction and an enzyme-substrate reaction, but also a method utilizing a combination thereof with an electric analysis has been attempted to achieve a high detection sensitivity.

For example, patent literature 1 discloses a combination of immunochromatography and a current-detection-type amperometric assay, and patent literature 2 discloses a biosensor in which a protein or an enzyme is immobilized on the gate of a field effect transistor or a single electron transistor. These prior art techniques are characterized by directly detecting a complex formed on the electrode or the gate by a specific interaction.

Further, methods utilizing deposition or adsorption on a sensor caused by a chemical reaction, instead of the utilization of a specific interaction, are disclosed in non-patent literature 1, patent literature 3, and patent literature 4.

Non-patent literature 1 discloses a method in which a silver ion dissolved in a reaction liquid is reduced to deposit silver on a sensor, the silver is reoxidized to generate a silver ion, and the electrochemical change during the reoxidization is detected as a change in current.

Patent literature 3 discloses a method for determining the concentration or amount of a substance to be assayed in a sample, using a labeled antibody in which cholinesterase is bound as a labeling enzyme and measuring the activity of the cholinesterase, wherein the enzyme activity is detected by adsorbing and concentrating an enzyme reaction product, thiocholine, on a noble metal electrode and amplifying the current signal generated by reduction desorption of the thiocholine from the electrode.

Patent literature 4 discloses an apparatus and a method for determining the production amount or the production rate of a thiol compound which is a product of a cyclic reaction of an enzyme-labeled antibody, as the adsorption rate on a gold electrode formed on an insulated gate field effect transistor.

In these prior art techniques, each chemical reaction and each electric detection are carried out under non-flow conditions.

Patent literature 5 discloses a biosensor for detecting a molecule involved in a specific binding of a biomolecule, characterized by comprising (i) a reaction part for carrying out (a) a specific binding reaction and (b) an enzyme reaction, (ii) a detection part for reacting an oxidation-reduction material membrane with the oxidation-reduction reaction product generated by reactions (a) and (b), and (iii) a measurement part for determining the change in dielectric constant by measuring a change in the state of the oxidation-reduction material membrane caused by the reaction thereof with the oxidation-reduction reaction product.

In this prior art technique, no deposit is generated on the sensor, in a similar to those disclosed in patent literatures 1 and 2.

[patent literature 1] Japanese Unexamined Patent Publication (Kokai) No. 2001-153838
[patent literature 2] Japanese Unexamined Patent Publication (Kokai) No. 10-260156
[patent literature 3] Japanese Unexamined Patent Publication (Kokai) No. 2004-257996
[patent literature 4] Japanese Unexamined Patent Publication (Kokai) No. 2007-263914
[patent literature 5] Japanese Unexamined Patent Publication (Kokai) No. 2005-24483
[non-patent literature 1] Analytical chemistry, (U.S.), 2005, vol. 77, p. 579-584

DISCLOSURE OF THE INVENTION

Problems to be Solved by the Invention

Although these prior art techniques are known, an analysis method with a higher detection sensitivity and accuracy is desired in order to measure a trace amount of a compound. Under the circumstances that it is technical common knowledge that these prior art methods utilizing deposition, precipitation or adsorption on the sensing part caused by chemical reactions in electric analysis methods should be carried out under non-flow conditions, from the viewpoint of promoting deposition and the like, the present inventors found that the detection sensitivity and accuracy can be significantly improved by carrying out the analysis under flow conditions, in contradiction to the technical common knowledge.

Therefore, an object of the present invention is to provide an analysis method with a higher detection sensitivity and accuracy than the prior art methods.

Means for Solving the Problems

The present invention relates to:
[1] an analysis method characterized by comprising the steps of:
 (a) reacting a substance to be analyzed with at least a specific partner which exhibits a selective interaction with the substance, converting a soluble substance to an insoluble substance by an insolubilization reaction, in correlation with the amount of the substance to be analyzed contained in a sample, and depositing the insoluble substance on a sensing part, and
 (b) electrically analyzing the insoluble substance deposited on the sensing part,
wherein at least one of steps (a) and (b) is carried out under flow conditions;
[2] the method of [1], wherein the specific partner is an enzyme;
[3] the method of [1], wherein step (a) comprises:
 (1) forming a complex comprising a substance to be analyzed, a specific partner which exhibits a selective interaction with the substance, and a labeling substance, in correlation with the amount of the substance to be analyzed contained in a sample, and
 (2) converting a soluble substance to an insoluble substance by an insolubilization reaction directly or indirectly caused by the labeling substance contained in the formed complex, and depositing the insoluble substance on a sensing part,
wherein at least one of steps (2) and (b) is carried out under flow conditions;

[4] the method of [3], wherein the labeling substance is a hydrolase;

[5] the method of [4], wherein the hydrolase is alkaline phosphatase;

[6] the method of [1] to [5], wherein the insolubilization reaction is an oxidation-reduction reaction;

[7] the method of [1] to [6], wherein the soluble substance is selected from an inorganic ion, an organic ion, an enzyme substrate or its reaction product, and a dye;

[8] the method of [7], wherein the soluble substance is a metal ion;

[9] the method of [8], wherein the metal ion is a silver ion;

[10] the method of [1] to [9], wherein the sensing part is composed of any one of a metal, a polymer, carbon, a nanotube structure, graphite, or inorganic substance, or a combination thereof;

[11] the method of [1] to [10], wherein the sensing part has one or more three-dimensional structures having an acute-angle-like shape;

[12] the method of [1] to [11], wherein the specific partner is immobilized on the sensing part;

[13] the method of [1] to [12], wherein the flow conditions are an enforced flow or a spontaneous flow;

[14] the method of [1] to [13], wherein the analysis method comprising the electric analysis step is an amperometric analysis;

[15] a sensing part which is used in the method of [1] to [14], and has one or more three-dimensional structures having an acute-angle-like shape;

[16] an reagent and kit for measuring a substance to be analyzed, characterized by using the method of [1] to [14], and comprising a specific partner which exhibits a selective interaction with the substance, a soluble substance which can be converted to an insoluble substance by an insolubilization reaction, and at least one of the sensing part described in any one of [1] to [15]; and

[17] the reagent and kit of [16], comprising the sensing part in the form of a cartridge for analysis having the sensing part.

Effects of the Invention

According to the present invention, analysis can be carried out with a higher detection sensitivity and accuracy in comparison with prior art.

BEST MODE FOR CARRYING OUT THE INVENTION

The present invention relates to an analysis method utilizing a selective interaction (for example, an antigen-antibody reaction or an enzyme-substrate reaction) and an insolubilization reaction (preferably an oxidation-reduction reaction), in which an insoluble substance which is finally produced by the insolubilization reaction is deposited (precipitated and adsorbed, insolubilized, or separated out) on the surface of a sensing part, and the deposited insoluble substance is electrically analyzed (detected or measured), and characterized in that at least one of the insolubilization reaction and the electric analysis is carried out under flow conditions.

In accordance with the selective interaction or the insolubilization reaction utilized, the present invention includes, for example, (1) a method in which an insolubilization reaction is directly or indirectly caused by a labeling substance capable of directly or indirectly labeling one of the partners which are involved in a selective interaction (hereinafter referred to as a complex-forming analysis method), and (2) a method in which an insolubilization reaction is directly or indirectly caused by a selective interaction per se (hereinafter referred to as an enzyme-utilizing analysis method). In this regard, the classification is based on whether or not a complex is formed by the selective interaction. For example, a method utilizing an enzyme as a labeling substance is included in the complex-forming analysis method.

The expression "an insolubilization reaction is directly caused" as used herein means that the reaction per se in which a labeling substance or a selective interaction participates is an insolubilization reaction, and an insoluble substance is generated by the reaction. The expression "an insolubilization reaction is indirectly caused" as used herein means a substance generated by the reaction in which a labeling substance or a selective interaction participates functions as a trigger, and an insoluble substance is generated by an insolubilization reaction which finally occurs.

Hereinafter, the outline of the present invention will be explained, based on the reaction scheme of FIG. 1 which shows an embodiment of the complex-forming analysis method of the present invention, and the present invention will be further explained in detail.

Figure 1:
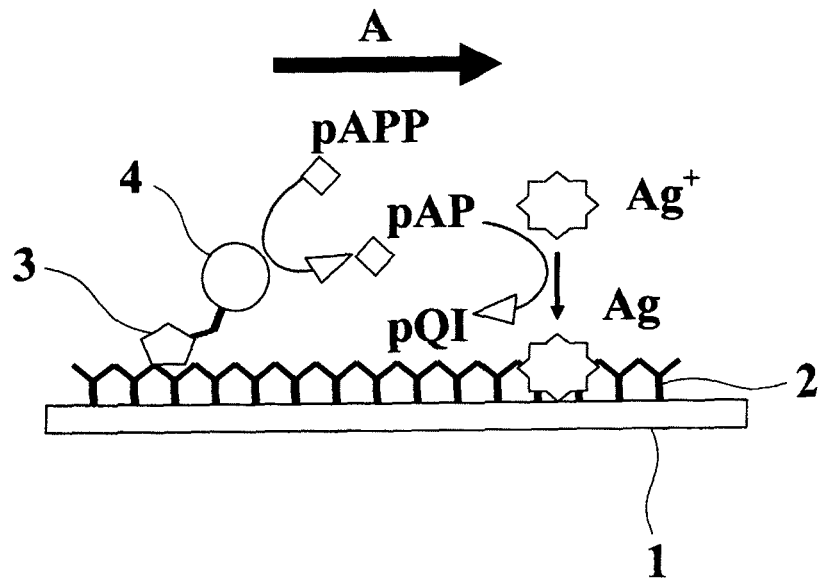
FIG. 1 is a drawing which shows a series of reactions utilizing in an embodiment of the analysis method of the present invention.

In the analysis system shown in FIG. 1, the antigen 3 is an analyte, an antigen-antibody reaction (sandwich method) is utilized as the selective interaction, and the ALP-labeled antibody 4 [an antibody which is specific to the antigen and is labeled with an enzyme such as alkaline phosphatase (ALP)] is used as a reagent.

In this analysis system, reaction formula 1 described below is utilized as the enzyme reaction of the labeling enzyme, and reaction formula 2 is utilized as the insolubilization reaction. In FIG. 1, pAPP represents p-aminophenylphosphate, pAP represents p-aminophenol, pQI represents p-quinone imine, and pAPP is a substrate of ALP. The description "(ALP)" in reaction formula 1 shows that ALP functions as a catalyst in reaction formula 1.

Further, as the electric analysis method, an amperometric analysis using an electrode part having a working electrode 1, a counter electrode, and a reference electrode is used.

p-aminophenylphosphate→p-aminophenol
(ALP)  (reaction formula 1)

p-aminophenol+2Ag⁺→p-quinone imine+
2H⁺+2Ag↓  (reaction formula 2)

Ag→Ag⁺+e⁻  (reaction formula 3)

In the analysis system shown in FIG. 1, an antibody 2 specific to the analyte (antigen) is immobilized on the working electrode 1 which constitutes an amperometric electrode part, and the working electrode functions as a sensing part. When a sample containing the analyte (antigen 3) and the ALP-labeled antibody 4 are supplied, along the flow direction represented by arrow A, from the upstream of the sensing part to the analysis system, a complex of immobilized antibody/antigen/ALP-labeled antibody is formed on the sensing part. The amount of complex formed correlates with the amount of the analyte contained in the sample. After the formation of the complex, or simultaneously with the formation, p-aminophenylphosphate (pAPP), a substrate for the labeling enzyme ALP, is supplied from the upstream of the sensing part to the analysis system. pAPP is converted to p-aminophenol (pAP) (reaction formula 1) and, in the presence of a silver ion (Ag⁺, water-soluble), silver (Ag, water-insoluble) is deposited (reaction formula 2) on the sensing part. Because a current runs from the working electrode to the counter electrode (reaction formula 3) by reoxidizing the silver deposited on the sensing part (working electrode), the amount of silver can be determined by measuring the oxidation current. More particularly, a potentiostat is connected to the working electrode, the counter electrode, and the reference electrode, and the electric potential of the working electrode is swept with respect to the reference electrode to measure the oxidation current accompanied by the reoxidization of silver.

The selective interaction which may be used in the present invention is not particularly limited, so long as it is an interaction in which one of the partners which participates in the interaction may be an analyte, and an insolubilization reaction can be directly or indirectly carried out or a complex can be formed, in correlation with the amount of the analyte contained in a sample. Typical examples of the selective interaction include an antigen-antibody reaction, a nucleic acid-nucleic acid hybridization reaction, an enzyme-substrate reaction, a nucleic acid-protein interaction, a receptor-ligand interaction, a protein-protein interaction (for example, a reaction of IgG with protein A), and a small molecule-protein interaction (for example, a reaction of biotin with avidin). These are mostly selective interactions capable of forming a complex (for example, an immunocomplex), but the enzyme-substrate reaction may be an insolubilization reaction in correlation with the amount of the analyte contained in a sample, or a reaction which triggers an insolubilization reaction.

In addition to these interactions, various combinations of a substance and its specific partner showing the selective interaction are known. Examples of the analyte include proteins (for examples, enzyme, antigen/antibody, lectin), peptides, lipids, hormones (nitrogen-containing hormones such as amines, amino acid derivatives, peptides, and proteins, and steroid hormones), nucleic acids, sugar chains (for example, sugars, oligosaccharides, and polysaccharides), drugs, dyes, small molecule compounds, organic substances, and inorganic substances; a fusion thereof; molecules which constitute a virus or a cell; and blood cells.

For example, when an antigen-antibody reaction is utilized as the selective interaction, the combination of an analyte and its specific partner may be a combination of an antigen (analyte) and an antibody (specific partner) or a combination of an antibody (analyte) and an antigen (specific partner). When an enzyme-substrate reaction is utilized as the selective interaction, the combination of an analyte and its specific partner may be a combination of a substrate (analyte) and an enzyme (specific partner) or a combination of an enzyme (analyte) and a substrate (specific partner).

As a sample containing the analyte, for example, blood (whole blood, plasma, serum), lymph, saliva, urine, feces, sweat, mucus, tears, cerebrospinal fluid, nasal discharge, cervical or vaginal secretion, semen, pleural fluid, amniotic fluid, ascites fluid, middle ear fluid, joint fluid, gastric aspirate, or various biological fluids such as extracts or homogenates derived from tissues or cells may be used. In addition, almost any liquid samples, such as extracts or homogenates derived from food, soil, or plants, river water, hot spring water, drinking water, and contaminated water, may be used.

In the present invention, reagents including a labeling reagent may be appropriately selected in accordance with the selective interaction used. For example, when an antigen-antibody reaction is utilized, various known methods such as a sandwich method, a two-step method, a competition method, and an inhibition method may be used. In the sandwich method, a combination of an immobilized partner and a labeled partner, as shown in FIG. 1, may be used. In the two-step method, a combination of an immobilized partner, an unlabeled partner, and a labeled substance which specifically reacts with the unlabeled partner, more particularly, a method using a first antibody and a labeled second antibody, or a method using a biotinylated antibody and a labeled avidin, may be used. In the competition method, a combination of a labeled substance (known amount) of an analyte (competitor) and an immobilized partner may be used.

The soluble substance which may be used in the present invention is not particularly limited, so long as it is soluble to a solvent used in the analysis system before an insolubilization reaction is carried out, it can be converted to a substance insoluble to the solvent by the insolubilization reaction, and the insoluble substance generated by the insolubilization reaction can be electrically analyzed. The term "insolubilization reaction" as used herein includes a reaction in which a substance having a low solubility is generated from a soluble substance by the "insolubilization reaction". The terms "soluble" and "insoluble" may be appropriately defined in accordance with a solvent system used in the analysis system. For example, when an aqueous solvent is used, the terms "soluble" and "insoluble" mean "water-soluble" and "water-insoluble". When an organic solvent is used, the terms "soluble" and "insoluble" mean "organic-solvent-soluble" and "organic-solvent-insoluble". Hereinafter, the present invention will be explained mainly in accordance with embodiments using an aqueous solvent (i.e., a system in which a water-soluble substance is converted to a water-insoluble substance by an insolubilization reaction), but those skilled in the art can carry out the present invention using a solvent other than water, by appropriately modify the embodiments.

The water-soluble substance which may be used in the present invention is not particularly limited, so long as it is soluble to an aqueous solvent used in the analysis system before an insolubilization reaction is carried out, and it can be converted to a substance insoluble to the aqueous solvent by the insolubilization reaction. Examples of the water-soluble substance include inorganic ions (preferably metal ions), organic ions, an enzyme substrate or its reaction product, and dyes.

Examples of the metal ions include antimony ion, bismuth ion, copper ion, mercury ion, silver ion, palladium ion, platinum ion, and gold ion. These metal ions are water-soluble to an aqueous solvent, and may form metal complexes (preferably metal complex ions), and are deposited as metals by an insolubilization reaction.

As the metal ion, divalent cations such as copper ion, nickel ion, and iron ion may be used. These divalent cations are water-soluble to an aqueous solvent, and are deposited as metal complexes ($MH[Fe(CN)_6]$ (M: divalent cation)) when binding with a $[Fe(CN)_6]^{3-}$ ion (for example, $[Fe(CN)_6]^{3-}$ ion generated by the oxidation of $[Fe(CN)_6]^{4-}$ ion).

A reaction in which a metal ion is reduced and insolubilized (deposited) as a metal is dependent on its oxidation-reduction potential. The lower the ionization tendency is, the more easily the metal is deposited, and thus, it is not limited to the above reactions. In addition, the ease of deposition may be considerably affected by the electrochemical activity of the ion in a solution and other factors (for example, temperature, pH, ion strength, and reaction liquid composition), and thus, the term "deposited metal" as used herein should be interpreted most broadly, and should not be restrictively interpreted. For example, the extent of the insolubility can be controlled by adding, to the insolubilization reaction system, an ion capable of forming an insoluble salt with the metal ion. Alternatively, it is sometimes preferable to insolubilize and deposit the metal ion as a metal, in the absence of the ion capable of forming an insoluble salt during the insolubilization reaction. The amount of the ion capable of forming an insoluble salt contained in the insolubilization reaction system can be appropriately selected by those skilled in the art. It may be 0 to 5 mmol/L, preferably 0 to 2 mmol/L, more preferably 0 to 1 mmol/L, and most preferably 0 to 0.5 mmol/L. The substance to be deposited is not limited to metal ions, but any substance which satisfies the above conditions can be preferably used.

Examples of the dye which may be used as the water-soluble substance include Schiff reagent and aniline. The Schiff reagent is water-soluble to an aqueous solvent. A molecule of Schiff reagent binds with two molecules of an aldehyde group (for example, aldehyde group generated by the reduction of a carboxyl group) and is deposited as a red-purple compound by a reduction reaction. Aniline is water-soluble to an aqueous solvent, and is deposited as polyaniline by an oxidation reaction.

Further examples of the water-soluble dye include 5-bromo-4-chloro-3-hydroxyindole (BCI), Nitro Blue Tetrazolium chloride (NBT), and indole, which are deposited by reduction as insoluble substances such as 5,5'-dibromo-4,4'-dichloro-indigo (2BCI), BCI/NBT diformazan, and indigo. These dyes may be generated from appropriate enzyme substrates, such as 5-bromo-4-chloro-3-indolyl phosphate (BCIP) and 3-indoxylphosphate, by an enzyme reaction by a labeling enzyme (for example, alkaline phosphatase; ALP). That is to say, BCI and indole are reaction products of enzyme substrates.

When the enzyme substrate BCIP is used, BCI is generated by an enzyme reaction in which ALP is involved, and 2BCI is deposited by a reduction reaction. When a mixture of the enzyme substrate BCIP and the dye NBT is used, 2BCI is generated by the enzyme reaction of ALP, and at the same time, NBT diformazan is generated by a reduction reaction, and as a result, a complex thereof, 2BCI/NBT diformazan, is deposited. When the enzyme substrate 3-indoxylphosphate is used, indole is generated by an enzyme reaction of ALP, and is deposited as indigo by a reduction reaction.

In these embodiments, an enzyme reaction in which ALP used as a labeling substance is involved triggers the subsequent insolubilization reaction, and as a result, a water-soluble substance is converted to a water-insoluble substance.

The present invention includes an embodiment in which a labeling substance functions as a trigger and the insolubilization reaction is indirectly caused, and an embodiment in which the insolubilization reaction is directly caused by the labeling substance.

Examples of the enzyme substrate which may be used as the water-soluble substance include, in addition to pAPP (or its derivatives) as described above, ester derivatives of thiocholine, such as acetylthiocholine, propionylthiocholine, succinylthiocholine, and butyrylthiocholine. When an ester derivative of thiocholine is used together with a metal ion described above (for example, gold or silver), the metal ion is reduced by an enzyme reaction using an appropriate labeling enzyme (for example, a cholinesterase such as acetylcholinesterase or acylcholinesterase) and deposited as a metal. Further, thiocholine is generated by the enzyme reaction, and the thiol group of the thiocholine binds with a part of the deposited metal, and as a result, the metal is also deposited as a metal-thiocholine complex. Furthermore, the generated thiocholine is also deposited by binding with a metal which forms an electrode or a substrate (for example, a gold electrode or a gold substrate) via the thiol group. A labeling enzyme acetylcholinesterase may be used for an enzyme substrate acetylthiocholine or propionylthiocholine, and a labeling enzyme acylcholinesterase may be used for an enzyme substrate succinylthiocholine or butyrylthiocholine.

Further, as the water-soluble substance, aryldiazonium salts such as $R\text{-}Ph\text{-}N_2BF_4$ may be used. When an aryldiazonium salt is used, an active radical having a high chemical activity is generated by a reduction reaction, and can bind with various sensing parts, preferably a detection part made of carbon, graphite, or carbon nanotubes, by covalent binding.

As above, the soluble substance (in particular, water-soluble substance) which may be used in the analysis method (including the complex-forming analysis method and the enzyme-utilizing analysis method) of the present invention are explained. In the complex-forming analysis method of the present invention, a labeling substance may be appropriately selected in accordance with the soluble substance and the reaction system used. For example, in addition to hydrolases such as ALP or cholinesterases described above, transferases, lyases, ligases, isomerases, and oxidoreductases may be used. Examples of oxidoreductases include glucose oxidase (GOD), peroxidase, xanthine oxidase, amino acid oxidase, ascorbate oxidase, acyl-CoA oxidase, cholesterol oxidase, galactose oxidase, oxalate oxidase, and sarcosine oxidase. These enzymes are not particularly limited, so long as they can directly or indirectly trigger an insolubilization reaction (for example, an oxidation reaction, a reduction reaction, a hydrolysis reaction, a dehydration reaction, addition polymerization, condensation polymerization, or a neutralization reaction), a soluble substance is converted to an insoluble substance by the insolubilization reaction, and a reaction of adsorption and/or deposition is caused by the deposition, binding, and/or precipitation on the surface of a solid body. These enzymes may be used alone, or as a combination of two or more enzymes.

In addition to these enzymes, various reducing agents or oxidizing agents may be used.

As the enzyme which may be used in the enzyme-utilizing analysis method of the present invention, an enzyme in which either the enzyme or its enzyme substrate is an analyte may be used. For example, from among the enzymes which may be used in the complex-forming analysis method, one or more enzymes may be selected.

The electric analysis method used in the present invention is not particularly limited, so long as an insoluble substance deposited on the surface of a sensing part is electrically analyzed. The term "electric analysis" as used herein includes, for example, an analysis in which a change in the charge on the surface of a sensing part is detected as a change in a current, an analysis in which a change in the charge on the surface of a sensing part is detected as a change in a voltage (electric potential), and an analysis in which the change is detected as a change in an electric resistance (or impedance). Examples of the electric analysis method used in the present invention include an amperometric analysis method using an electrode part having at least a working electrode and a counter electrode, and a voltammetric analysis method using a transistor.

In the amperometric analysis method, a change in the charge on the surface of a sensing part is detected as a change in a current. An amperometric electrode part comprises at least a working electrode and a counter electrode on a substrate, and may further comprise a reference electrode if desired. In the amperometric analysis method, the amount of an electrode active material or a resistant material (insulating material) generated near the electrode part is determined by measuring a current signal which flows between the working electrode and the counter electrode in correlation with the amount of the material by applying a predetermined voltage between both electrodes, or the difference in an electrode active material or a resistant material (insulating material) generated near the electrode part is detected by a voltage value applied between the working electrode and the counter electrode.

For example, when a metal ion is used as the water-soluble substance, a voltage is applied to a sensing part on which the metal is deposited, with respect to the reference electrode, and as a result, the metal deposited on the sensing part is reoxidized to the metal ion, and the electrochemical change on the sensing part can be detected as a change in a current.

As a method other than amperometry for detecting a change in a current, for example, cyclic voltammetry, differential pulse voltammetry, chronoamperometry, and differential pulse amperometry, which are widely-known, may be used.

In the voltammetric analysis method, a change in the charge on the surface of a sensing part is detected as a change in a voltage (potential). The transistor used in the voltammetric analysis method is a device which converts voltage signals inputted to a gate into current signals output from a source electrode or a drain electrode. When a voltage is applied between the source electrode and the drain electrode, charged particles existing in the channel formed between both electrodes move along an electric field direction between both electrodes, and are output as a current signal from the source electrode or the drain electrode. In this case, the strength of the output current signal is proportional to the density of the charged particles. When a voltage is applied on the gate which is placed at upward, sideward or downward position of the channel with an insulator therebetween, the density of the charged particles existing in the channel is changed. With the aid of this property, the current signal can be varied by changing the gate voltage.

For example, when acetylthiocholine is used as the water-soluble substance, a change in the charge on the sensing part caused by thiocholine, which is deposited on the sensing part by acetylcholinesterase, can be detected as a change in a voltage (potential).

With respect to a preferred embodiment of the sensing part, when the sensing part is conductive, conductive materials such as metals (for example, gold, silver, platinum, rhodium, ruthenium, iridium, mercury, and palladium), polymers (for example, an osmium polymer), carbon, a nanotubular structure (carbon nanotubes), graphite or inorganic substances may be used, alone or as a combination thereof. The shape of the structure made of these materials is not particular limited, so long as the structure does not inhibit the reaction, and may be a plane shape, projections and depressions, or particles (for example, gold colloid).

A preferred embodiment of the nanotubular structure is a structure selected from the group consisting of carbon nanotubes, boron nitride nanotubes, and titania nanotubes.

The sensing part may contain nonconductive materials in addition to the conductive materials, so long as the sensing part shows a conductive property. As the nonconductive materials, for example, an insoluble carrier made of polyester resins may be used.

Another preferred embodiment of the sensing part is a gate electrode of a field effect transistor or a single-electron transistor using a nanotubular structure (carbon nanotubes). This nanotubular structure is preferably a structure selected from the group consisting of carbon nanotubes, boron nitride nanotubes, and titania nanotubes.

As still another preferred embodiment of the sensing part, a porous carrier such as a nitrocellulose membrane used in immunochromatography, a polymer as described in WO 2006/038456, or an insoluble carrier (or insoluble particles) such as a latex carrier may be used, to increase the surface area of the sensing part, and further, a three-dimensional structure may be formed on the surface of the sensing part using conductive materials such as conductive polymers or a conductive carrier. The three-dimensional structure formed on the surface of the sensing part can significantly increase the surface area of the sensing part, and as a result, the detection sensitivity can be improved.

With respect to another preferred shape of the sensing part, to improve the efficiency of the deposition (precipitation and adsorption, insolubilization, or separation out) of a product generated on the sensing part under flow conditions, or to avoid the removal of the deposited (insolubilized, separated-out, or precipitated) product from the sensing part along the flow direction (for example, toward the downstream) under flow condition, wells, projections and depressions, projections, or partitions may be formed on the sensing part. By forming these structures on the sensing part, it also can be expected that the reactivity of the deposited product will be improved. The structure may be formed only on the sensing part, or on the electrode part or the biosensor unit so that a part thereof exists on the sensing part.

More particularly, a shape having one or more three-dimensional structures having a acute-angle-like shape is preferable. Examples of the shape include a polyhedron, polygonal prism, sphere, cylinder, cone, and pyramid, and a cone or a pyramid is preferred. At least one three-dimensional structure having one or more acute parts or projections may be formed on the sensing part, and it is preferable to form multiple three-dimensional structures on the sensing part. The number and the size of the three-dimensional structures, the number of the acute parts, and the shape and the arrangement thereof can be appropriately selected in accordance with the measurement conditions. The terms "acute-angle-like shape" and "acute part" as used herein are not particularly limited, so long as a part or the whole of the three-dimensional structure formed on the sensing part has an edge effect. The edge effect, which is a well-known effect in a technical field such as electroplating, is the effect that the charges concentrate at acute edges. It is considered that a deposited (insolubilized)

metal such as silver is actively reionized to a metal ion by this effect, and that the detection sensitivity can be improved.

The selective interaction reaction between an analyte and its specific partner is carried out at the place on which the specific partner is immobilized. The place where the specific partner is immobilized is not particularly limited, so long as the selective interaction is carried out, and then an electric measurement can be carried out. The surface of the sensing part is preferable.

The method for immobilizing the specific partner is not particularly limited, and any method, such as a direct immobilization method or an indirect immobilization method, may be used in accordance with the properties of the selective interaction reaction. For example, the specific partner may be directly immobilized on the substrate by physical adsorption or covalent binding, or indirectly immobilized via a flexible spacer having an anchor previously bound to the substrate. For example, if a rare metal such as gold is used as the substrate, the specific partner may be immobilized to the substrate via a self-assembled monolayer.

After the immobilization of the specific partner, the inhibition of nonspecific reactions or the selection or control of a permeable substance can be achieved, by treating the surface with bovine serum albumin, polyethylene oxide, or other inactive molecules, or by coating the immobilized layer with an additive layer.

In the enzyme-utilizing analysis method of the present invention, insolubilization reaction step (a), which is based on the selective interaction, and electric analysis step (b) are carried out. In the complex-forming analysis method of the present invention, complex-forming step (a1), which is based on the selective interaction, insolubilization reaction step (a2), which is based on a labeling substance contained in the complex, and electric analysis step (b) are carried out. These steps are generally carried out in these orders, but contiguous steps (or parts thereof) may be simultaneously carried out, so long as an electric signal which correlates with the amount of the analyte contained in a sample can be obtained. In the present invention, at least one of the insolubilization reaction step and the electric analysis step is carried out under flow conditions.

The term "under flow conditions" as used herein means that the supply of a fresh liquid for reaction to the interface of the desired reaction part in the reaction system, and the discharge of a reaction liquid after the reaction can be simultaneously and continuously or intermittently carried out, successively through the whole process of the step. It is preferable that the reaction part "under flow conditions" is the insolubilization reaction part in which step (a) or step (a2) is carried out, and/or the sensing part in which step (b) is carried out. The flow is not limited to one direction, and may be reciprocating, vibration, or convection in the desired step to proceed with a desired reaction.

For example, in a batch method, a predetermined amount of liquid for reaction is supplied at a time, a desired reaction is carried out for a predetermined period of time and, after the reaction, the reaction liquid is discharged. By contrast, in the present invention, the supply of a liquid for reaction and the discharge of the reaction liquid proceed simultaneously. In the present invention, it is usual that the supply and the discharge is simultaneously carried out continuously through the whole process of a desired step, but the supply and the discharge may be simultaneously carried out intermittently (i.e., with a temporary halt in supply and discharge), so long as the effects of the present invention can be sufficiently obtained.

The flow conditions include an enforced flow and a spontaneous flow. Examples of the enforced flow include flows caused by mechanical, electric, or manual methods, such as pumping, centrifuging, stirring, sonication, and application of magnetism, and flows utilizing pressure, vacuum, or vibration caused by pressing. Examples of spontaneous flow include capillary action and free fall. These flows may be used in various channels of a microfabricated flow, lateral flow, capillary flow, or flow-through, or a membrane strip for immunochromatography or the like.

The flow rate under flow conditions in the present invention is not particularly limited, so long as the insoluble substance generated can be deposited on the sensing part, and there is a non-zero flow (i.e., not in the static state). The flow rate varies in accordance with various conditions, for example, the selective interaction or the insolubilization reaction utilized, the labeling substance, the soluble substance, or the oxidation-reduction substance used, the size of the flow channel, or the electric analysis method used. However, those skilled in the art can appropriately determine the flow rate, for example, by carrying out an easy preliminary experiment in accordance with the procedures shown in Examples described below, without undue experimentation.

As previously described in the "PROBLEMS TO BE SOLVED BY THE INVENTION" section, it was technical common knowledge at the time of filing of the present application that various prior art methods utilizing deposition, precipitation or adsorption on the sensing part caused by chemical reactions are carried out under non-flow conditions, from the viewpoint of promoting deposition and the like. The reason why the detection sensitivity and accuracy can be significantly improved by carrying out the present invention under flow conditions in comparison with non-flow conditions, in contradiction to the technical common knowledge, is not clarified at this point in time, but the present inventors assume the following mechanism. In this regard, the present invention is not limited to the speculation.

When, for example, a silver ion is used as the water-soluble substance as the reaction shown in FIG. 1, an enzyme substrate and the silver ion are consumed during the oxidation-reduction reaction. It is assumed that the sensitivity is improved because a fresh enzyme substrate and silver ion are supplied under flow conditions, in comparison with non-flow conditions. Further, it is assumed that the sensitivity is improved because a silver ion generated near the sensing part by reoxidizing the deposited silver to silver ion is removed therefrom under flow conditions, and thereby the reaction rate in the reoxidation of silver is improved. Furthermore, it is assumed that the sensitivity is synergistically improved because both reactions proceed simultaneously.

EXAMPLES

The present invention will now be further illustrated by, but is by no means limited to, the following Examples.

Example 1

Figure 2:
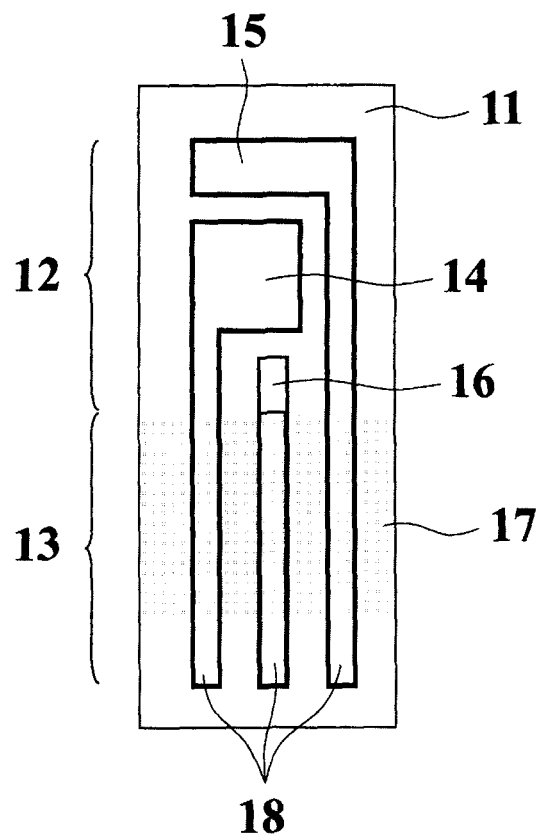
FIG. 2 is a plan view schematically showing the electrode part constructed in Example 1.
Figure 3:
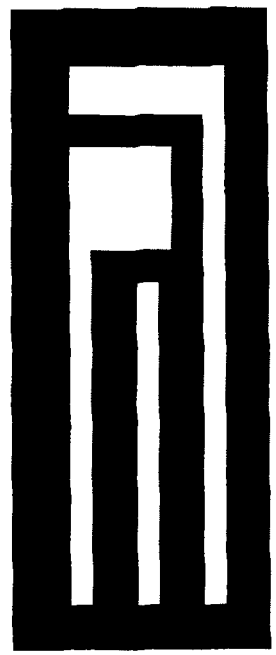
FIG. 3 is a plan view schematically showing the mask pattern used in the construction of the electrode part shown in FIG. 2.
Figure 4:
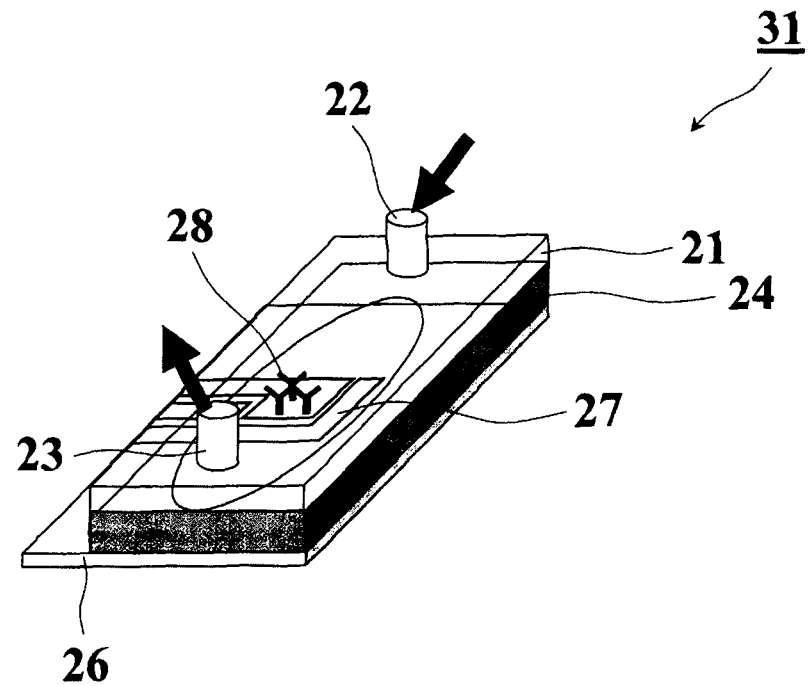
FIG. 4 is a perspective view schematically showing the biosensor unit constructed in Example 1.
Figure 5:
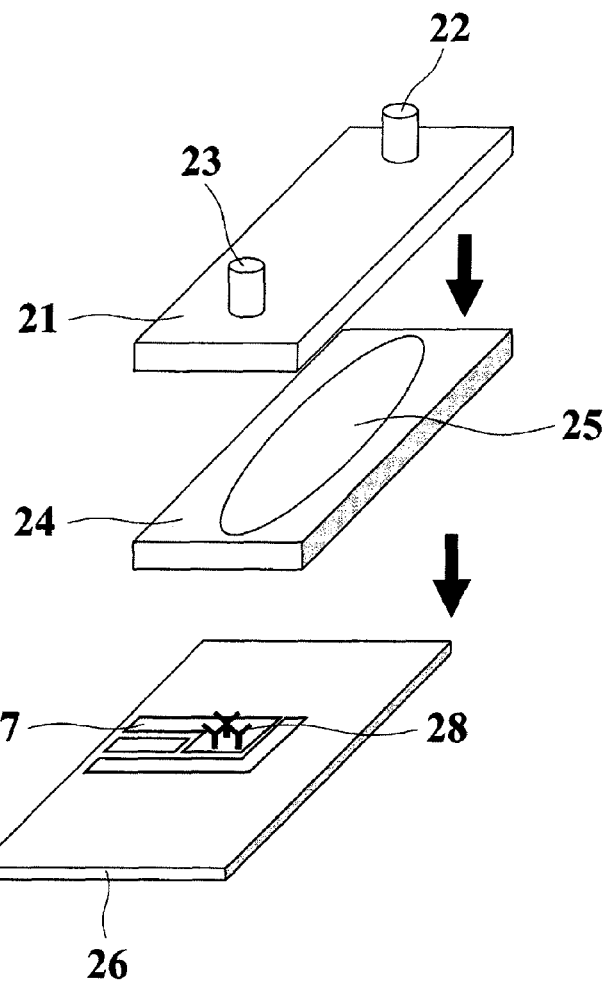
FIG. 5 is a drawing which schematically shows the production process of the biosensor unit shown in FIG. 4.
Figure 6:
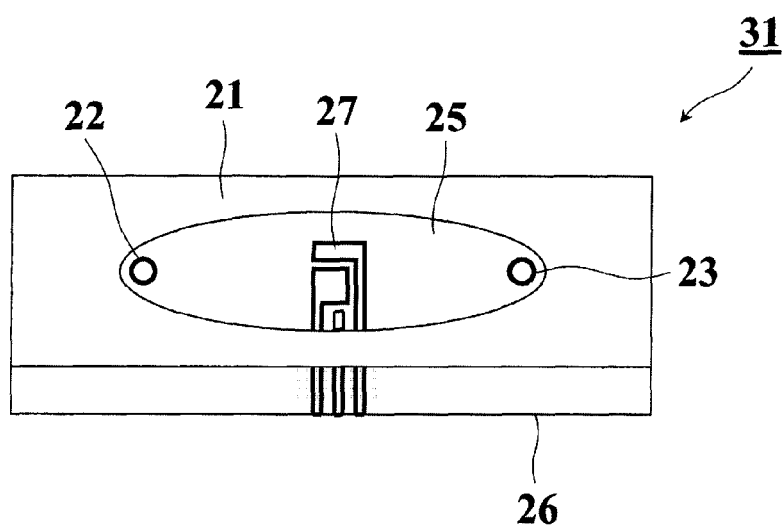
FIG. 6 is a plane view schematically showing the biosensor unit shown in FIG. 4.
Figure 7:
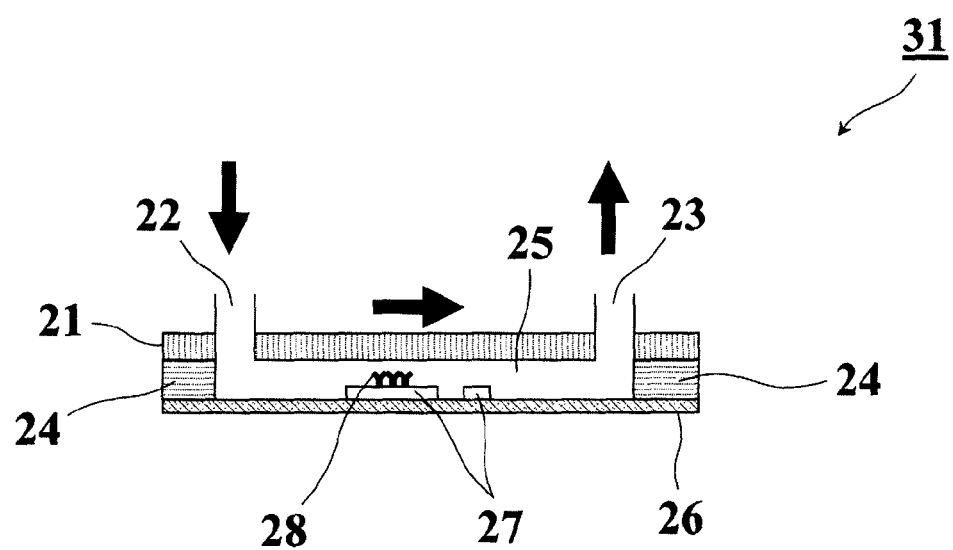
FIG. 7 is a cross-sectional view schematically showing the internal structure of the biosensor unit shown in FIG. 4.

Measurement of Hepatitis B Surface Antigen (HBsAg) Using Gold Electrodes 1-1. Construction of Electrode Part and Sensing Part An electrode part having a pattern as shown in FIG. 2 was constructed, using a mask pattern as shown in FIG. 3, by a sputtering method and a lift-off method. A gold thin film having a thickness of 50 nm was formed on an insulating substrate 11 made of polyethylene terephthalate (PET), and a silver/silver chloride ink (manufactured by BAS Inc.) was applied on a part of the gold thin film to construct a reference electrode 16. To divide the area between the electrode part 12 and a lead part 13, a part of the lead part was covered with an insulating layer 17 to construct the electrode part having a working electrode 14, a counter electrode 15, and the reference electrode 16. The ends opposite to the working electrode, the counter electrode, and the reference electrode function as connectors 18. The working electrode contained in the electrode part functions as a sensing part.

1-2. Construction of Interaction Reaction Part and Insolubilization Part

An aqueous solution (2 μL) containing an antibody specific to a hepatitis B surface antigen (HBs antigen), an anti-HBs monoclonal antibody (IgG; In-house product), was put on to the working electrode of the electrode part formed on the substrate, and was allowed to stand at 37° C. under saturated vapor pressure for 30 minutes to immobilize the antibody on the working electrode. The aqueous solution was prepared so that the concentration of the antibody was adjusted to 1 mg/mL in a 0.1 mol/L phosphate buffer (pH 7.4) containing 0.15 mol/L NaCl (hereinafter referred to as buffer A). The substrate was dried at 25° C. and a humidity of 40% for an hour, and further dried in a vacuum desiccator at room temperature for 2 hours. The dried substrate was immersed in a 0.1 mol/L Tris buffer (pH 8.0) containing 1% casein (manufactured by Wako Pure Chemical Industries, Ltd.) and 0.15 mol/L NaCl for 30 minutes while shaking, to block the part with which the antibody had not reacted. The blocked substrate was washed with desalted water, and dried. By taking these steps, the anti-HBs monoclonal antibody as a specific substance was immobilized on the working electrode (sensing part) to construct an interaction reaction part and an insolubilization part (oxidation-reduction reaction part) on the working electrode.

1-3. Preparation of Solution Containing Anti-HBs Rabbit Polyclonal Antibody (Fab') Labeled with Alkaline Phosphatase (ALP)

An anti-HBs rabbit polyclonal antibody (Fab') labeled with ALP was prepared, in accordance with the maleimide hinge method described in "Kokando koso meneki sokutei-hou (Ultrasensitive enzyme immunoassay), Eiji ISHIKAWA, Japan Scientific Societies Press, 1993", using an anti-HBs rabbit polyclonal antibody (in-house product), ALP (manufactured by Roche), and a crosslinking reagent (Succinimidyl 4-[N-maleimidomethyl]-cyclohexane-1-carboxylate; manufactured by PIERCE). The resulting enzyme-labeled antibody [ALP-labeled anti-HBs rabbit polyclonal antibody (Fab')] was dissolved in buffer A and adjusted to a predetermined concentration, to prepare an ALP-labeled anti-HBs antibody solution.

1-4. Preparation of Substrate Solution Containing Silver Ion

As a substrate solution containing silver ion, a 0.05 mol/L diethanolamine solution (pH 9.4) containing 2 mmol/L p-aminophenylphosphate (pAPP; manufactured by LKT Laboratories), 0.125 mmol/L $AgNO_3$, 0.5 mmol/L $MgSO_4$, 0.25 mmol/L $MgCl_2$, and 0.075 mol/L NaCl was prepared.

1-5. Preparation of Substrate Solution without Silver Ion (pAPP Substrate Solution; for Control Experiment)

As a pAPP substrate solution, a 0.05 mol/L diethanolamine solution (pH 9.4) containing 2 mmol/L pAPP, 0.5 mmol/L $MgSO_4$, 0.25 mmol/L $MgCl_2$, and 0.075 mol/L NaCl was prepared.

1-6. Construction of Flow Channel and Apparatus for Controlling Flow Conditions

A biosensor unit as shown in FIGS. 4 to 7 was constructed. As shown in FIGS. 4 to 7, a window 21 made of a glass plate having two holes (openings) as an inlet 22 and an outlet 23 for reaction solution, and the previously-constructed substrate 26 having the electrode part 27 on which the anti-HBs monoclonal antibody 28 was immobilized, were used to sandwich a gasket 24 made of a double-sided tape (thickness=0.64 mm; manufactured by 3M) having a slot for flow channel, to construct the biosensor unit 31, in which the electrode part was disposed in the hollow flow channel 25.

Figure 8:
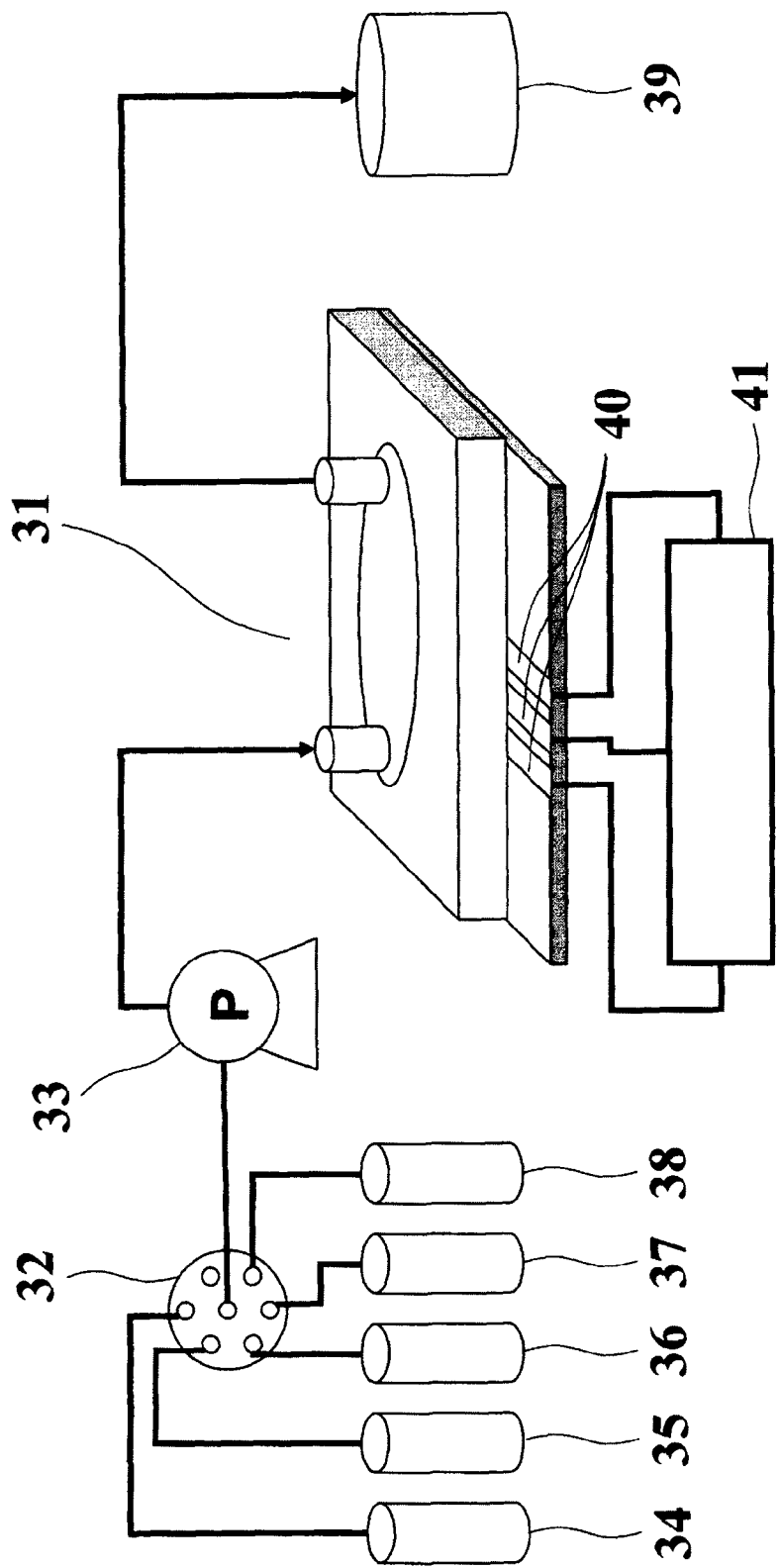
FIG. 8 is a perspective view schematically showing the biosensor shown in FIG. 4 connected to an apparatus for controlling flow conditions and an electrochemical analyzer.

At the inlet side of the biosensor unit 31, as shown in FIG. 8, liquid (reagent) servers 34 to 38, a switching valve 32 (EV100-105; manufactured by GL Sciences Inc.), and a pump 33 (PERISTALTIC PUMP P-1; manufactured by former Pharmacia) were connected via tubes, and a waist liquid server 39 was connected to the outlet of the flow channel. Using this system, each solution (samples, reagents, or buffers) supplied from the reagent servers can be passed through the flow channel at a desired flow rate in the direction from the inlet to the outlet.

1-7. Measurement of HBs Antigen by Electrochemical Analyzer

The constructed biosensor unit and the apparatus for controlling flow conditions were used to carry out the measurement of HBs antigen. Buffer A (reagent server 1) was passed through the flow channel for 2 minutes. After this, by switching the switching valve, an HBs antigen solution [prepared by diluting HBs antigen (recombinant, subtype adw; in-house product) with buffer A to a predetermined concentration] (reagent server 2) was passed through the flow channel for 30 minutes. The valve was switched to pass the ALP-labeled anti-HBs antibody solution (2 μg/mL) (reagent server 3) through the flow channel for 30 minutes. Further, the valve was switched to pass the substrate solution containing silver ion (reagent server 4) or the pAPP substrate solution (reagent server 5) through the flow channel for 4 minutes, and electrochemical measurements were carried out while maintaining the flow conditions.

Each electrochemical measurement was carried out, as shown in FIG. 8. More particularly, the connectors 40 to the working, reference, and counter electrodes were connected to an electrochemical analyzer 41 (model 832A; manufactured by ALS). The electric potential was varied between −0.15 V and 0.6 V with respect to the reference electrode, while passing the substrate solution containing silver ion or the pAPP substrate solution through the flow channel, to measure the electrochemical response by cyclic voltammetry (CV).

1-8. Results of Measurements (1) Detection of Oxidation Current Caused by the Presence of HBs Antigen (Compound to be Measured)

Figure 9:
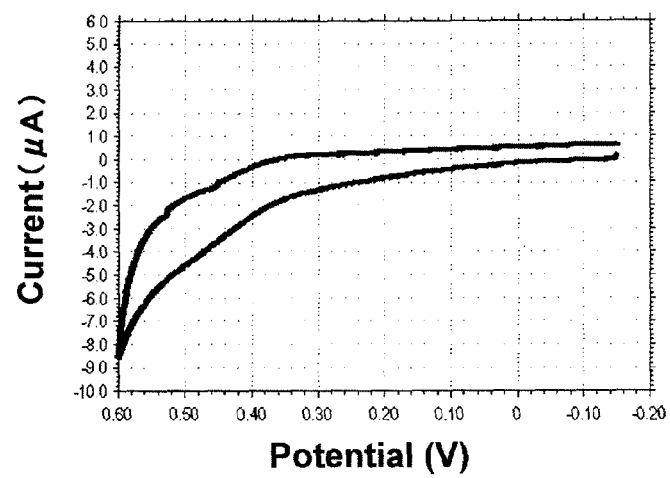
FIG. 9 is a graph showing the result of a CV measurement of HBs antigen (concentration of antigen=0 U/mL).
Figure 10:
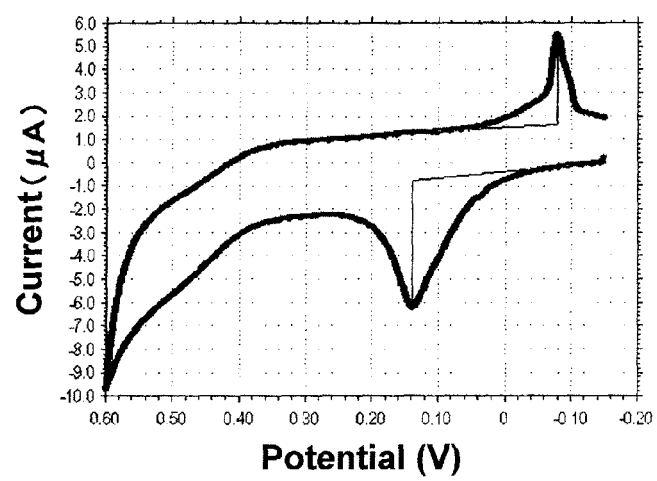
FIG. 10 is a graph showing the result of a CV measurement of HBs antigen (concentration of antigen=48 U/mL).

The result of a CV measurement where the concentration of HBs antigen was 0 U/mL is shown in FIG. 9, and the result of a CV measurement where the concentration of HBs antigen was 48 U/mL is shown in FIG. 10. The feed of liquid to the flow channel (i.e., flow conditions) was carried out at a flow rate of 360 μL/min through the whole process (from the feed of buffer A for 2 minutes to the electrochemical measurement).

When the concentration of HBs antigen was 48 U/mL (FIG. 10), as an oxidation current accompanied by an oxidation reaction of deposited silver, an oxidation current of 5.44 μA was detected at an electric potential of +0.138 V (oxidation potential) with respect to the reference electrode. By contrast, when the concentration of HBs antigen was 0 U/mL (FIG. 9), no similar oxidation current was detected.

Figure 11:
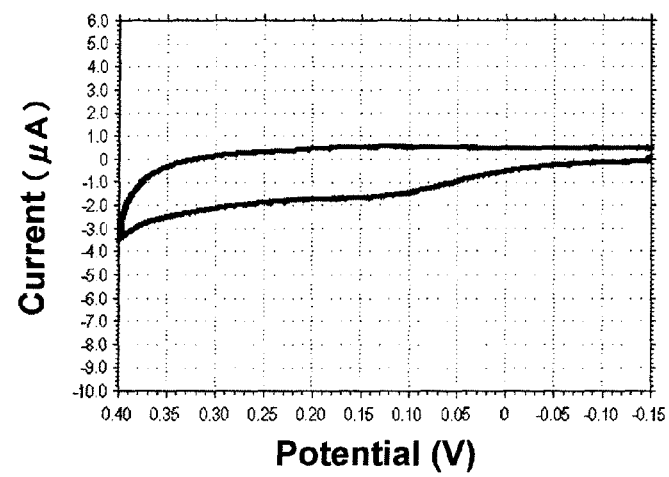
FIG. 11 is a graph showing the result of a CV measurement of HBs antigen (concentration of antigen=48 U/mL) in the absence of a silver ion.

(2) Relationship Between the Presence of Silver Ion and the Detection of Oxidation Current In this experiment, it was examined whether or not the presence or absence of silver ion affected the silver deposition. FIG. 11 shows the result of a CV measurement which was carried out under the same conditions as those in FIG. 10

(concentration of HBs antigen: 48 U/mL, flow rate: 360 μL/min), except that the pAPP substrate solution (i.e., not containing silver ion) was used instead of the substrate solution containing silver ion.

According to the comparison of the results shown in FIGS. 10 and 11, when the substrate solution containing silver ion was used (FIG. 10), as an oxidation current accompanied by an oxidation reaction of deposited silver, an oxidation current of 5.44 μA was detected at an electric potential of +0.138 V (oxidation potential) with respect to the reference electrode. By contrast, when the pAPP substrate solution was used (FIG. 11), an oxidation current derived from p-aminophenol (pAP) as its product was not clearly detected. It was found from this result that the detection sensitivity of HBs antigen could be significantly improved under flow conditions by the deposition of silver or the like as a product of the reaction.

(3) Effect of Flow Rate on Oxidation Current

In this experiment, to examine the effect of flow conditions (flow rate), each oxidation current at an electric potential of +0.138 V with respect to the reference electrode was measured when the flow rate was changed to 0, 200, 360, and 1260 μL/min. The measurements were carried out under the same conditions as those in FIG. 8 (concentration of HBs antigen: 48 U/mL), except for the flow rate.

The result is shown in Table 1. As apparent from Table 1, it was found that the reactivity significantly increased under flow conditions, when compared to the conditions where the flow rate was 0 μL/min (non-flow conditions).

TABLE 1

| Flow rate (μL/min) | Oxidation current (μA) |
|---|---|
| 0 | 0.498 |
| 200 | 1.42 |
| 360 | 5.17 |
| 1260 | 3.01 |

(4) Confirmation of Quantitative Properties

In this experiment, to examine the quantitative properties in the measurement of HBs antigen, each oxidation current at an electric potential of +0.138 V with respect to the reference electrode was measured when the concentration of HBs antigen was changed to 0, 24, and 48 U/mL. The measurement was carried out under the same conditions as those in FIG. 10 (flow rate: 360 μL/min), except for the concentration of HBs antigen.

Figure 12:
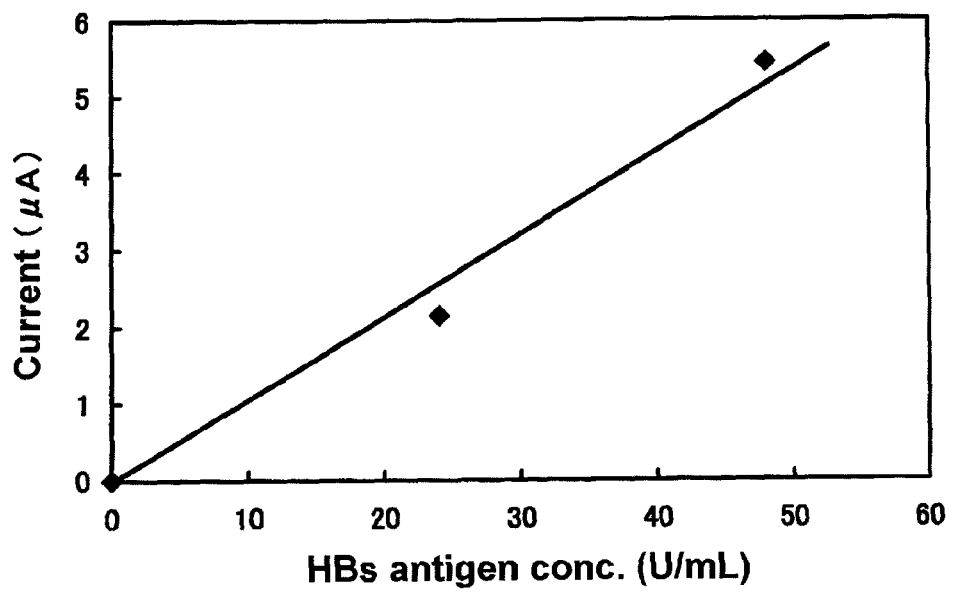
FIG. 12 is a graph showing oxidation current values at an electric potential of +0.138 V obtained in CV measurements of various concentrations of HBs antigen (concentrations of antigen=0, 24, and 48 U/mL).

The result is shown in FIG. 12. As apparent from FIG. 12, the current increased dependent on the concentration of HBs antigen, and the quantitative properties were confirmed.

Example 2

Measurement of Glucose Using Glucose Oxidase (GOD)

2-1. Construction of Electrode Part and Sensing Part

An electrode part was constructed in accordance with the procedure described in item 1-1 of Example 1. The working electrode contained in the electrode part functions as a sensing part.

2-2. Construction of Interaction Reaction Part and Insolubilization Part

An aqueous solution (2 μL) containing 2000 U/mL GOD (Roche) in buffer A was put on to the working electrode of the electrode part, and was allowed to stand at 37° C. under saturated vapor pressure for 30 minutes to immobilize the GOD on the working electrode. To remove the solvent, the substrate was dried at 25° C. and a humidity of 40% for an hour, and further dried in a vacuum desiccator at room temperature for 2 hours. The dried substrate was immersed in a 0.1 mol/L Tris buffer (pH 8.0) containing 1% casein (manufactured by Wako Pure Chemical Industries, Ltd.) and 0.15 mol/L NaCl for 30 minutes while shaking, to block the part with which the GOD had not reacted. The blocked substrate was washed with desalted water, and dried. As described above, the GOD as a specific substance was immobilized on the working electrode (sensing part) to construct an interaction reaction part and an insolubilization part on the working electrode.

2-3. Preparation of Solution Containing Silver Ion

As a solution containing silver ion, an aqueous solution (pH 9.0) containing 0.25 mmol/L $AgNO_3$ and 1 mmol/L $MgSO_4$ was prepared.

2-4. Preparation of Glucose Solution

As a glucose solution, a 0.1 mol/L diethanolamine solution (pH 9.8) containing 0.5 mmol/L $MgCl_2$, 0.15 mol/L NaCl, and a predetermined concentration of glucose was prepared.

2-5. Construction of Flow Channel and Apparatus for Controlling Flow Conditions

A flow channel and an apparatus for controlling flow conditions were constructed in accordance with the procedure described in item 1-6 of Example 1, except that the substrate (described in item 2-2) having the electrode part on which the GOD was immobilized, instead of the electrode part on which the anti-HBs monoclonal antibody was immobilized, was used.

2-6. Measurement of Glucose by Electrochemical Analyzer

The constructed biosensor unit and the apparatus for controlling flow conditions were used to carry out the measurement of glucose. Buffer A (reagent server 1) was passed through the flow channel for 2 minutes. After this, by switching the switching valve, a mixed solution (reagent server 2) of the silver-ion-containing solution and the glucose solution was passed through the flow channel at a flow rate of 1.26 mL/min for 5 minutes, and electrochemical measurements were carried out while maintaining the flow conditions. For this test, the mixed solution was prepared immediately before the switching, by mixing the silver-ion-containing solution and the glucose solution, which had been adjusted to a predetermined concentration, at a ratio of 1:1.

Each electrochemical measurement was carried out as follows. The connectors for the working, reference, and counter electrodes were connected to an electrochemical analyzer (model 832A; manufactured by ALS). The electric potential was varied between −0.15 V and 0.6 V with respect to the reference electrode, while passing the mixed solution through the flow channel, to measure the electrochemical response by cyclic voltammetry (CV).

Figure 13:
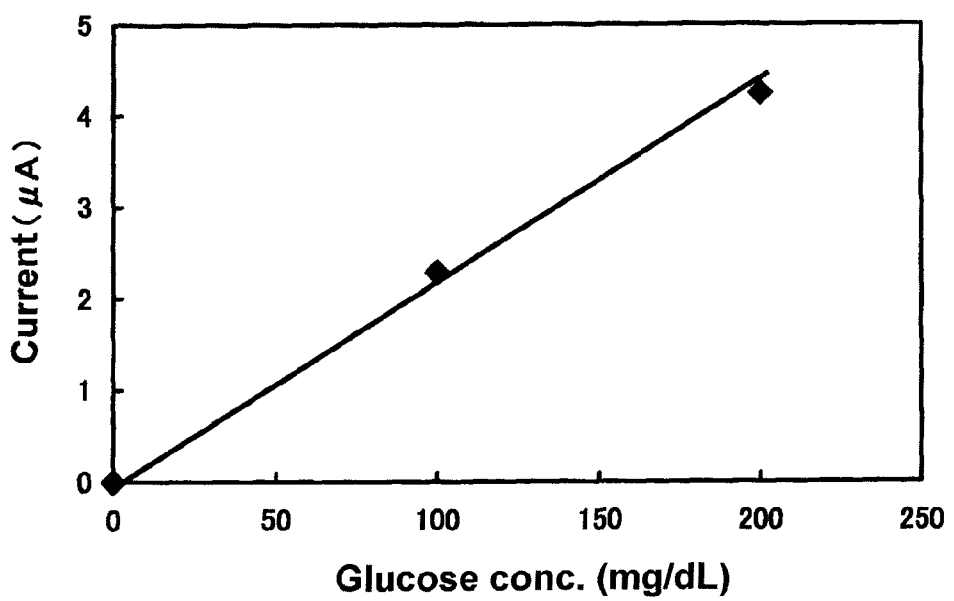
FIG. 13 is a graph showing oxidation current values at an electric potential of +0.086 V obtained in CV measurements of various concentrations of glucose (concentrations of glucose=0, 100, and 200 mg/dL).

2-7. Results of Measurements (1) Detection of Oxidation Current Dependent on Glucose Concentration The concentration of glucose contained in the mixed solution was changed to 0, 100, and 200 mg/dL, and for each a CV measurement was carried out. The oxidation currents accompanied by an oxidation reaction of deposited silver at an electric potential of +0.086 V with respect to the reference electrode are shown in FIG. 13. From among these results, the result of the CV measurement where the concentration of glucose contained in the mixed solution was 0 mg/dL (i.e., not containing glucose) is shown in FIG. 14, and the result of the CV measurement where the concentration of glucose was 200 mg/dL is shown in FIG. 15.

Figure 14:
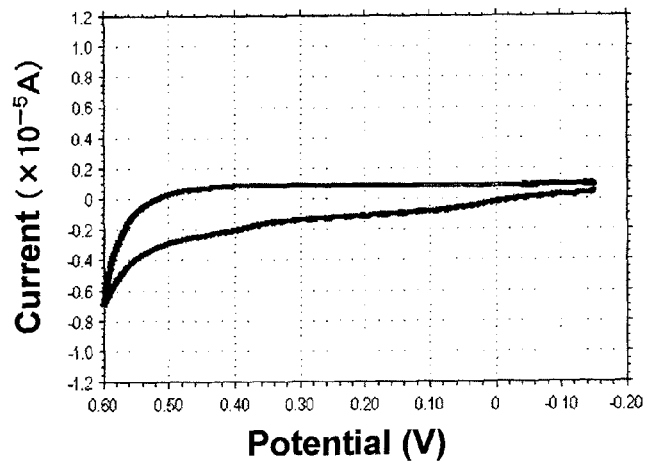
FIG. 14 is a graph showing the result of a CV measurement of glucose (concentration of glucose=0 mg/dL).
Figure 15:
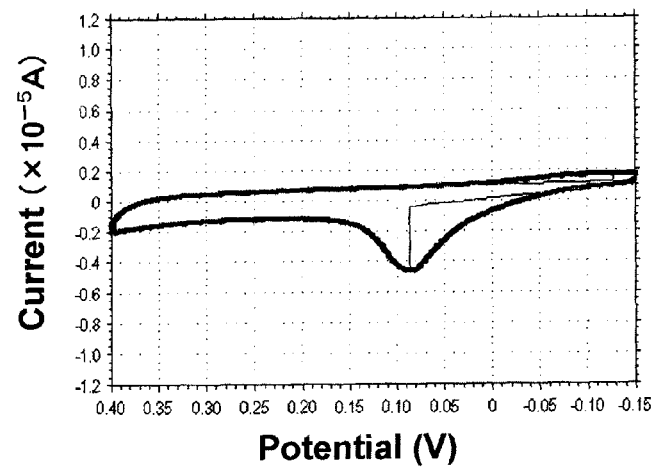
FIG. 15 is a graph showing the result of a CV measurement of glucose (concentration of glucose=200 mg/dL).

According to the comparison of FIGS. 14 and 15, when the concentration of glucose was 200 mg/dL (FIG. 15), as an oxidation current accompanied by an oxidation reaction of deposited silver, an oxidation current of 4.24 µA was detected at an electric potential of +0.086 V (oxidation potential) with respect to the reference electrode. By contrast, when the concentration of glucose contained in the mixed solution was 0 mg/dL (FIG. 14), no similar oxidation current was detected. Further, as shown in FIG. 13, the quantitative properties were confirmed.

(2) Effect of Flow Rate on Oxidation Current

Figure 16:
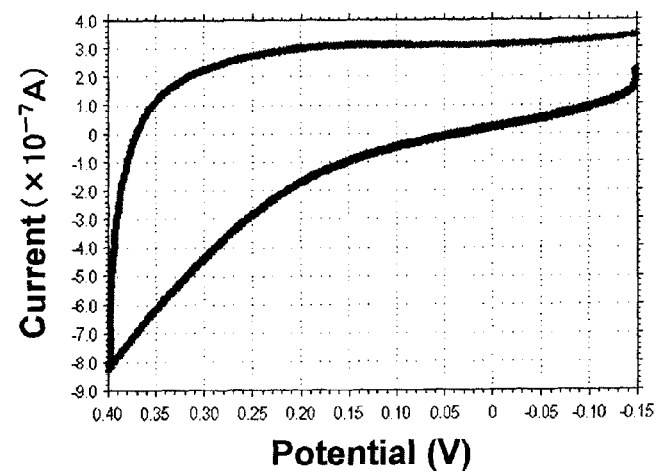
FIG. 16 is a graph showing the result of a CV measurement of glucose (concentration of glucose=0 mg/dL) under non-flow conditions.
Figure 17:
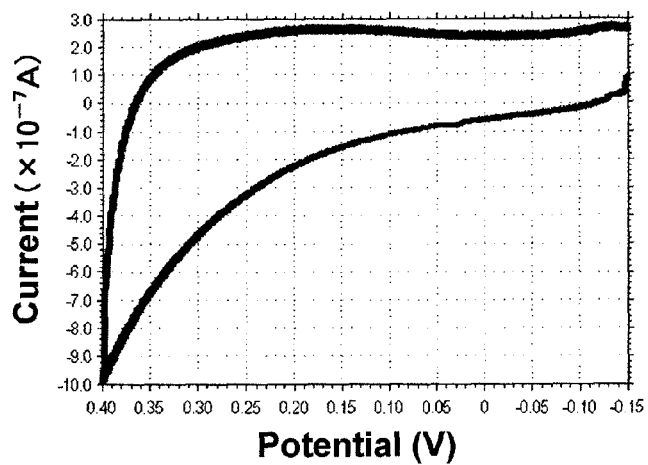
FIG. 17 is a graph showing the result of a CV measurement of glucose (concentration of glucose=200 mg/dL) under non-flow conditions.

In this experiment, to examine the effect of flow conditions (flow rate), each oxidation current was measured when the flow rate was 0 mL/min (standing; non-flow conditions) and the concentration of glucose contained in the mixed solution was 0 mg/dL and 200 mg/dL. A CV measurement was carried out while the electric potential was varied between −0.15 V and 0.4 V with respect to the reference electrode. The result of the CV measurement where the concentration of glucose contained in the mixed solution was 0 mg/dL (without glucose) is shown in FIG. 16, and the result of the CV measurement where the concentration of glucose was 200 mg/dL is shown in FIG. 17. No change in the oxidation current caused by the change in glucose concentration was detected between FIGS. 16 and 17. From the result that an oxidation current was detected under flow conditions at a glucose concentration of 200 mg/dL as shown in FIG. 15, whereas no similar oxidation current was detected at a flow rate of 0 mL/min (standing; non-flow conditions) (FIGS. 16 and 17), it was found that the measurement sensitivity of glucose could be significantly improved under flow conditions by the deposition of silver or the like as a product of the reaction.

(3) Confirmation of Effect of Non-Specific Reduction Reaction

Figure 18:
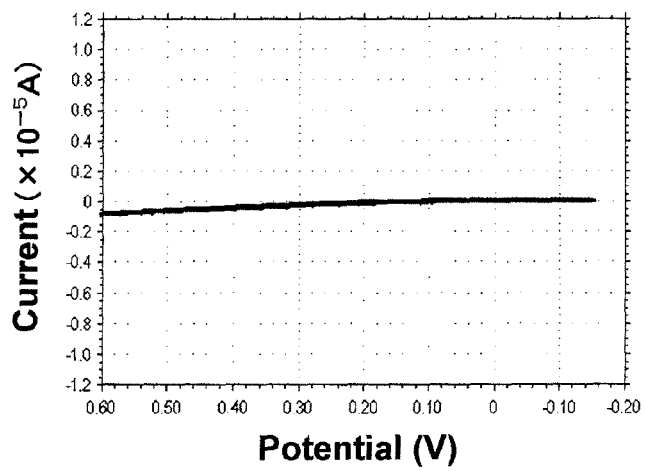
FIG. 18 is a graph showing the result of a CV measurement of glucose (concentration of glucose=200 mg/dL) using an electrode part in which GOD is not immobilized on the working electrode.

In this experiment, to examine the effect of a non-specific reduction reaction of silver ion by glucose under flow conditions, a biosensor having an electrode part in which GOD was not immobilized on the working electrode was used to measure the oxidation current at a glucose concentration of 200 mg/dL under the same conditions as used previously. The result of the CV measurement is shown in FIG. 18. As apparent from FIG. 18, no oxidation current derived from the non-specific deposition of silver was detected at the flow rate used in this Example.

Example 3

Influence and Effect of Flow Conditions at Each Step (1) Effect of Flow Conditions on Oxidation Current The influence and effect of flow condition were examined at step (A) of converting a soluble substance to an insoluble substance by an insolubilization reaction (oxidation-reduction reaction) and depositing the insoluble substance on a sensing part, or at step (B) of electrically analyzing the insoluble substance deposited on the sensing part. The biosensor and the apparatus for controlling flow conditions constructed in Example 1 were used to measure HBs antigen under the following three types of flow conditions.

Figure 19:
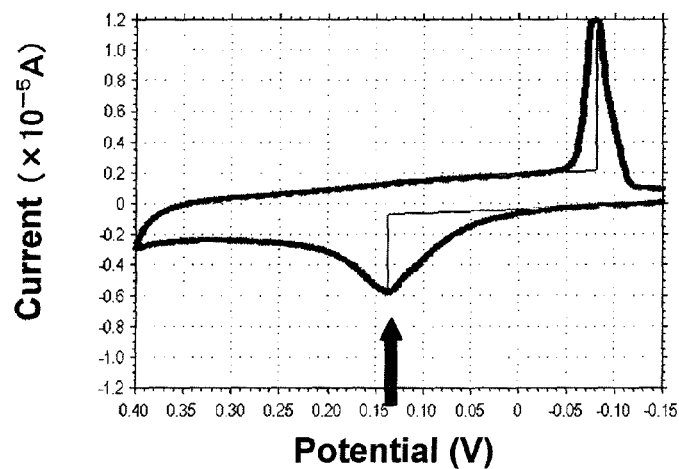
FIG. 19 is a graph showing the result of a CV measurement of HBs antigen under condition 1 (step A/step B=flow/flow) described in Example 3.
Figure 20:
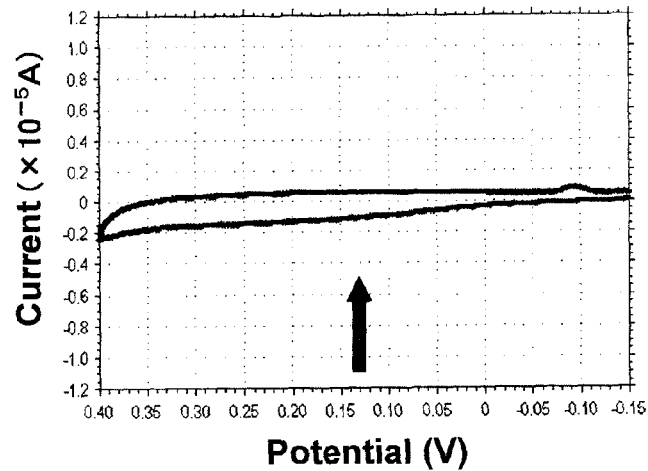
FIG. 20 is a graph showing the result of a CV measurement of HBs antigen under condition 2 (step A/step B=flow/non-flow) described in Example 3.
Figure 21:
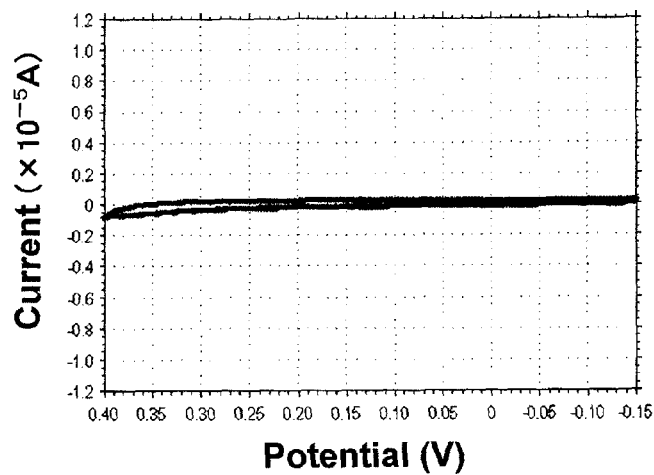
FIG. 21 is a graph showing the result of a CV measurement of HBs antigen under condition 3 (step A/step B=non-flow/non-flow) described in Example 3.

Buffer A (reagent server 1) was passed through the flow channel for 2 minutes. After this, by switching the switching valve, the HBs antigen solution (concentration of HBs antigen: 48 U/mL) (reagent server 2) was passed through the flow channel for 30 minutes. The valve was switched to pass the ALP-labeled anti-HBs antibody solution (2 µg/mL) (reagent server 3) through the flow channel for 30 minutes, to form a complex of the HBs antigen and the ALP-labeled anti-HBs antibody. Further, the valve was switched to pass the substrate solution containing silver ion (reagent server 4) through the flow channel. As "condition 1", the flow rate was maintained at 360 µL/min for 4 minutes (step A: flow), and an electrochemical measurement was carried out while maintaining the flow conditions (step B: flow). As "condition 2", the flow rate was maintained at 360 µL/min for 4 minutes (step A: flow), and an electrochemical measurement was carried out after the flow rate was changed to 0 µL/min (stopped) (step B: non-flow). As "condition 3", the flow rate was changed to 0 µL/min (stopped) and maintained for 4 minutes (step A: non-flow), and an electrochemical measurement was carried out while the flow rate was maintained at 0 µL/min (stopped) (step B: non-flow). Each electrochemical measurement was carried out while the electric potential was varied between −0.15 V and 0.4 V with respect to the reference electrode. The results of the CV measurement under conditions 1 to 3 are shown in FIGS. 19 to 21, respectively.

As a result, no oxidation current was detected under condition 3 (non-flow/non-flow; FIG. 21). An oxidation current of 0.78 µA was detected at an electric potential of +0.137 V with respect to the reference electrode under condition 2 (flow/non-flow; FIG. 20), and an oxidation current of 5.08 µA was detected under condition 3 (flow/flow; FIG. 19). From these results, it was found: that it was necessary to carry out at least one of steps A and B under flow conditions; that, in view of the comparison of condition 3 (FIG. 21) and condition 2 (FIG. 20), the HBs antigen could be detected when step A of depositing the reaction product on the sensing part was carried out under flow conditions: and that, in view of the comparison of condition 1 (FIG. 19) and condition 2 (FIG. 20), the detection sensitivity of HBs antigen could be significantly improved when the electrochemical measurement in step B was carried out under flow conditions.

Example 4

Measurement of HBs Antigen by Chromatography (Spontaneous Flow Method)

4-1. Construction of Electrode Part and Sensing Part

An electrode part was constructed in accordance with the procedure described in item 1-1 of Example 1. The working electrode contained in the electrode part functions as a sensing part.

4-2. Construction of Interaction Reaction Part and Insolubilization Part

An interaction reaction part and an insolubilization part were constructed on the working electrode in accordance with the procedure described in item 1-2 of Example 1.

4-3. Preparation of Reagent Solutions

Each reagent solution was prepared in accordance with the procedures described in items 1-3 and 1-4 of Example 1.

4-4. Construction of Immunochromatography (1) Construction of Electrode Part Immobilized with a Complex of Alp-Labeled Anti-HBs Rabbit Polyclonal Antibody/HBs Antigen/Anti-HBs Monoclonal Antibody (ALP-Labeled HBs Complex)

The anti-HBs-monoclonal-antibody-immobilized-electrode part constructed in item 4-2 was immersed in an HBs antigen solution [prepared by diluting HBs antigen (recombinant, subtype adw; in-house product) with buffer A to a predetermined concentration] while shaking. After this reaction was carried out for 30 minutes, the electrode part was washed with a desalted water, and air-dried. The dried electrode part was immersed in the ALP-labeled anti-HBs antibody solution (2 µg/mL) while shaking. After this reaction was carried out for 30 minutes, the electrode part was washed with a desalted water and air-dried to obtain an electrode part immobilized with an ALP-labeled HBs complex.

(2) Construction of Immunochromatography Having Electrode Part

Figure 22:
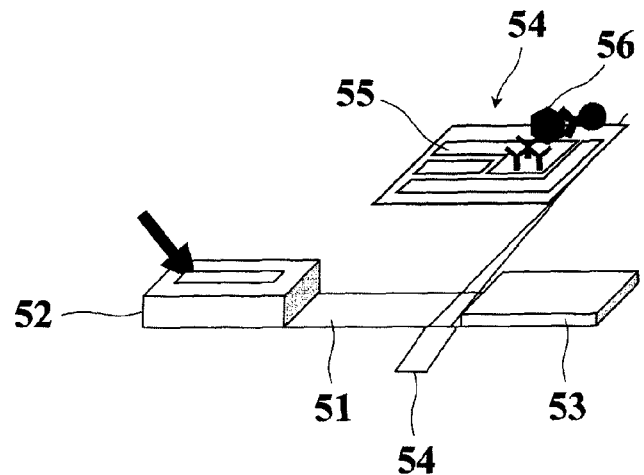
FIG. 22 is a drawing which schematically shows the structure of the immunochromatographic strip having an electrode part, constructed in Example 4.
Figure 23:
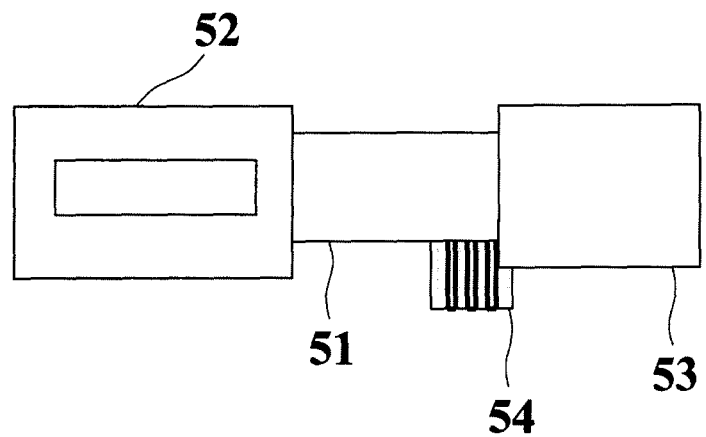
FIG. 23 is a schematic plan view of the immunochromatographic strip having an electrode part shown in FIG. 22.
Figure 24:
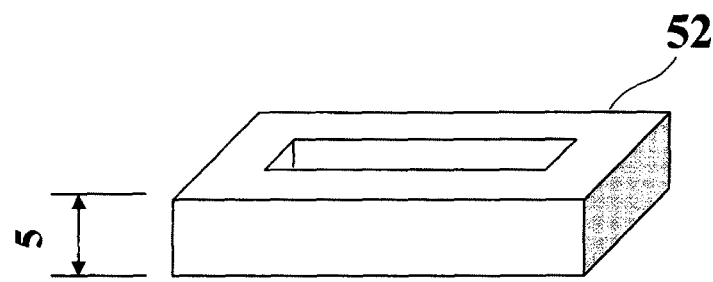
FIG. 24 is a perspective view (dimension units: mm) schematically showing a reservoir for applying a reagent, which is a component of the immunochromatographic strip having an electrode part shown in FIG. 22.
Figure 25:
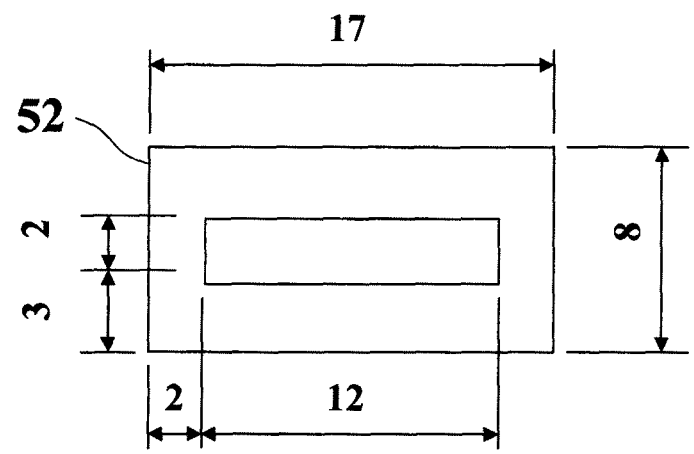
FIG. 25 is a plan view (dimension units: mm) schematically showing the reservoir for applying a reagent shown in FIG. 24.

An immunochromatography having an electrode part was constructed as follows. As shown in FIGS. 22 and 23, a nitrocellulose membrane (Hi-Flow 180 Unbacked; manufactured by MILLIPORE) 51 was cut to a size of 5 mm×40 mm, and a reservoir for applying a reagent 52, prepared by cutting a silicone rubber sheet (thickness: 5 mm, SR sheet SR-50; manufactured by Tigers Polymer Corporation) to the size as shown in FIGS. 24 and 25, was positioned on one end side (A end) of the membrane. On another end side (B end) of the membrane, a cellulose pad (CELLULOSE FIBER SAMPLE PADS; manufactured by MILLIPORE), cut to a size of 10 mm×30 mm as an absorbing pad 53, was attached to the membrane so that they were overlapped with each other at a width of 10 mm. On the backside of the nitrocellulose membrane at a position 10 mm from the B end, the electrode part immobilized with the ALP-labeled HBs complex 54 prepared in item (1), in which the ALP-labeled HBs complex 56 was immobilized on the electrode part 55, was arranged, so that the electrode part was brought into contact with the membrane, to obtain an immunochromatographic strip having an electrode part. By using this immunochromatographic strip having an electrode part, reactions under spontaneous flow conditions utilizing the capillarity in the nitrocellulose membrane can be electrically measured.

4-5. Measurement of HBs Antigen by Electrochemical Analyzer

The HBs antigen was measured using immunochromatographic strips having an electrode part, which had been prepared by changing the concentration of HBs antigen to 0, 18, and 36 U/mL. To the reagent-applying reservoir of each immunochromatographic strip having an electrode part, 150 µL of the substrate solution containing silver ion was added. This solution was transferred in the direction toward the B end by capillarity for 6 minutes, and electrochemical measurements were carried out while maintaining this status.

Each electrochemical measurement was carried out as follows. The connectors for the working, reference, and counter electrodes were connected to an electrochemical analyzer (model 832A; manufactured by ALS). The electric potential was varied between −0.15 V and 0.4 V with respect to the reference electrode to measure the electrochemical response by cyclic voltammetry (CV).

Figure 26:
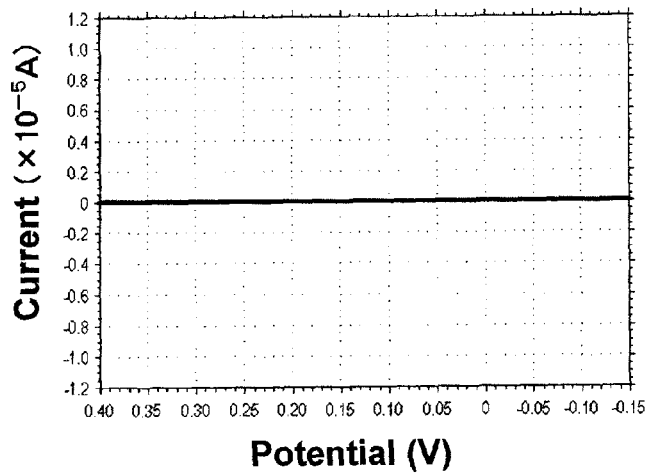
FIG. 26 is a graph showing the result of a CV measurement of HBs antigen (concentration of antigen=0 U/mL).
Figure 27:
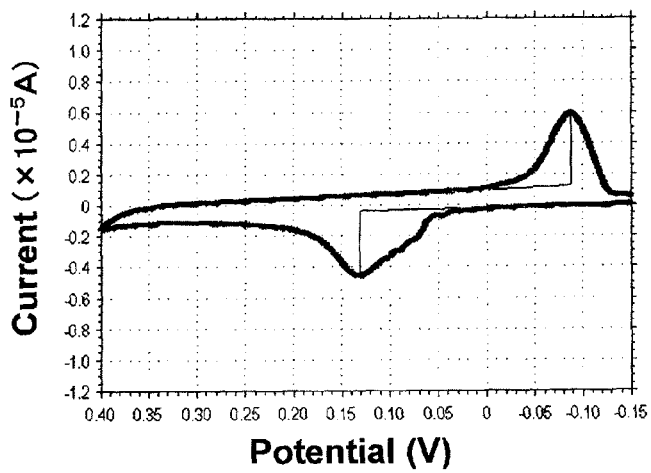
FIG. 27 is a graph showing the result of a CV measurement of HBs antigen (concentration of antigen=18 U/mL).
Figure 28:
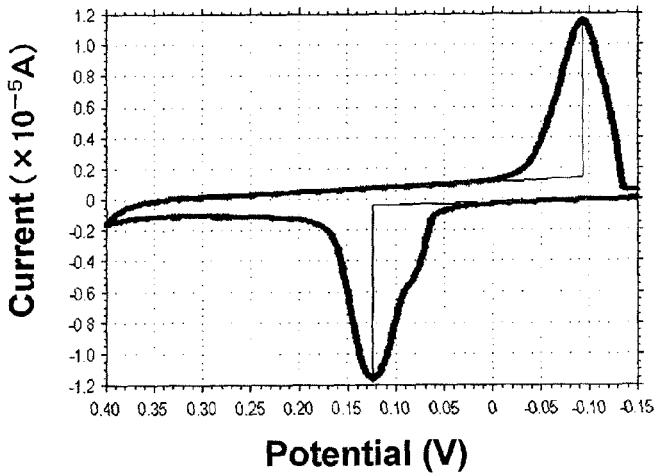
FIG. 28 is a graph showing the result of a CV measurement of HBs antigen (concentration of antigen=36 U/mL).
Figure 29:
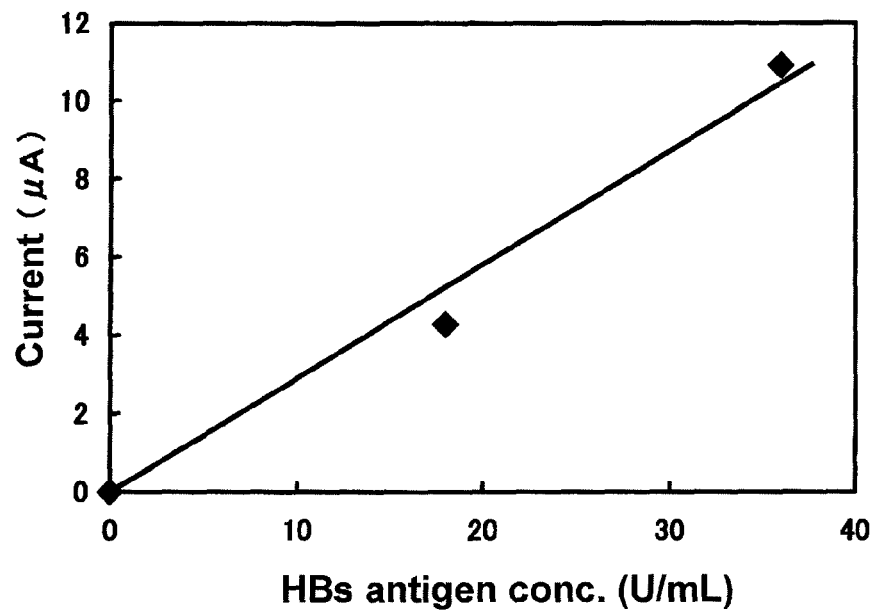
FIG. 29 is a graph showing oxidation current values at an electric potential of +0.132 V obtained in CV measurements of various concentrations of HBs antigen (concentrations of antigen=0, 24, and 48 U/mL).

4-6. Results of Measurements (1) Detection of Oxidation Current Caused by the Presence of HBs Antigen The results of CV measurements where the concentration of HBs antigen was 0, 18, and 36 U/mL are shown in FIGS. 26 to 28, respectively. No signal was detected when the concentration of HBs antigen was 0 U/mL. An oxidation current of 4.27 µA was detected at an electric potential of +0.132 V with respect to the reference electrode when the concentration was 18 U/mL. An oxidation current of 11.2 µA was detected at an electric potential of +0.124 V with respect to the reference electrode when the concentration was 36 U/mL. The result of the measurement of the oxidation current at an electric potential of +0.132 V with respect to the reference electrode is shown in FIG. 29. As apparent from FIG. 29, the oxidation current increased dependent on the concentration of HBs antigen, and thus, it was confirmed that the HBs antigen could be quantitatively measured by this method.

Example 5

Measurement of Hepatitis B Surface Antigen (HBsAg) Using Carbon Electrodes 5-1. Construction of Electrode Part and Sensing Part An electrode part having a pattern as shown in FIG. 2 was constructed, using a stainless steel mask pattern as shown in FIG. 3, by a printing method. An electrode structure was formed by printing a conductive carbon paste (FTU-20; Asahi Chemical Research Laboratory Co., Ltd.) on an insulating substrate 11 made of polyethylene terephthalate (PET). A silver/silver chloride ink (manufactured by BAS Inc.) was applied on a part of the electrode structure and heated at 120° C. for 10 minutes to construct an electrode part 12 and a reference electrode 16 (hereinafter sometimes referred to as the carbon electrode part). The ends opposite to the working electrode, the counter electrode, and the reference electrode function as connectors 18. The working electrode contained in the electrode part functions as a sensing part.

5-2. Construction of Interaction Reaction Part and Insolubilization Part

An interaction reaction part and an insolubilization part were constructed in accordance with the procedure described in Example 1-2.

5-3. Preparation of Solution Containing Anti-HBs Rabbit Polyclonal Antibody (Fab') Labeled with Alkaline Phosphatase (ALP)

A solution containing an anti-HBs rabbit polyclonal antibody (Fab') labeled with alkaline phosphatase (ALP) was prepared, in accordance with the procedure described in Example 1-3.

5-4. Preparation of Substrate Solution Containing Silver Ion

As a substrate solution containing silver ion, a 0.04 mol/L diethanolamine solution (pH 9.4) containing 2 mmol/L p-aminophenylphosphate (pAPP; manufactured by Universal sensors), 0.125 mmol/L $AgNO_3$, and 1 mmol/L $MgSO_4$ was prepared.

5-5. Preparation of Washing Solution

As a washing solution, a 0.04 mol/L diethanolamine solution (pH 9.4) containing 1 mmol/L $MgSO_4$ was prepared.

5-6. Construction of Capillary Flow Channel Having Carbon Electrode Part

Figure 30:
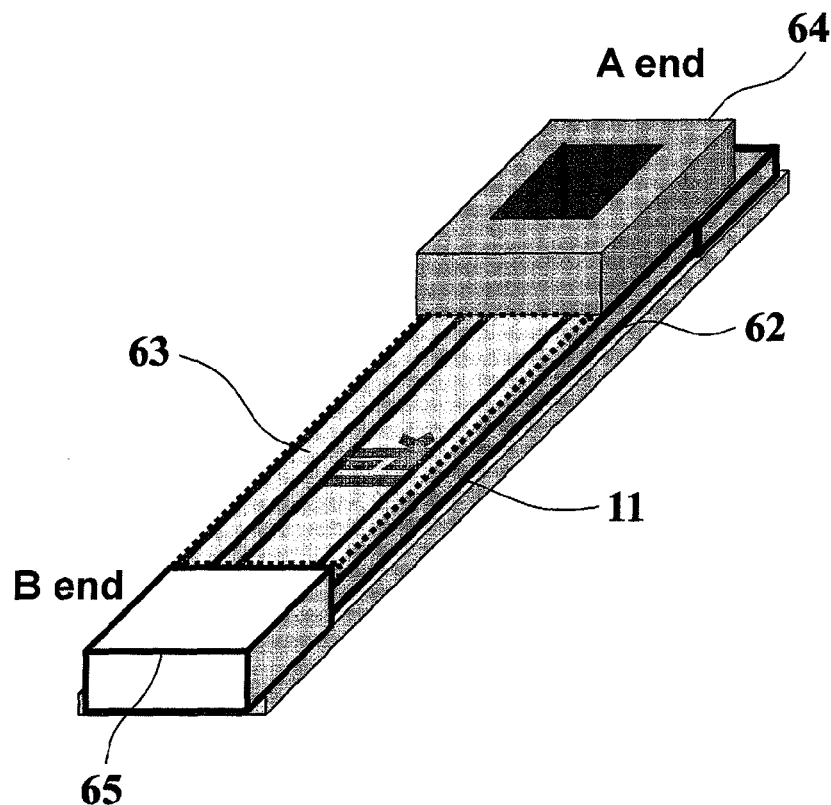
FIG. 30 is a perspective view schematically showing the capillary flow channel having an electrode part, constructed in Example 5.

As shown in FIG. 30, a capillary flow unit having the electrode part was constructed.

Figure 31:
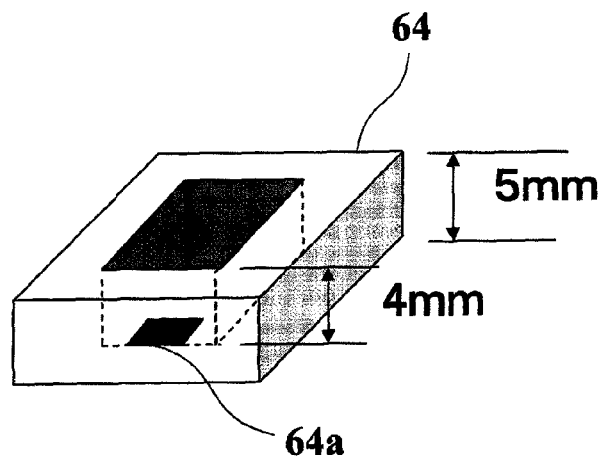
FIG. 31 is a perspective view (dimension units: mm) schematically showing a reservoir for applying a reagent, which is a component of the capillary flow channel having a carbon electrode part shown in FIG. 30.
Figure 32:
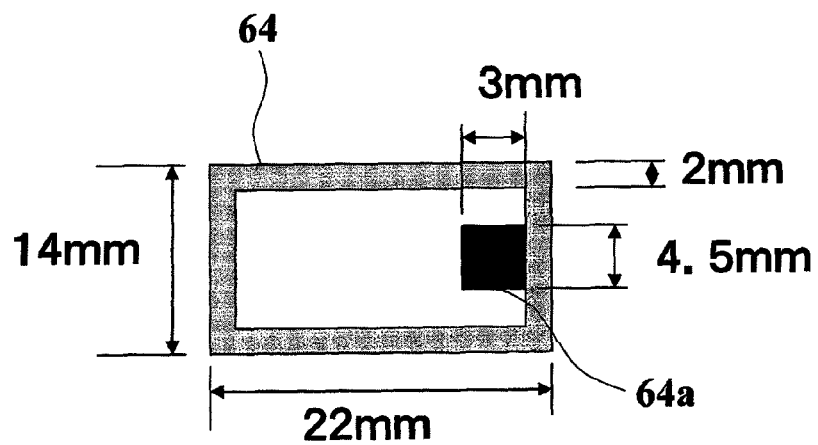
FIG. 32 is a plan view (dimension units: mm) schematically showing the reservoir for applying a reagent shown in FIG. 30.

As shown in FIG. 30, sections of double-sided tape 62 (Scotch ST416; manufactured by 3M) were arranged in parallel on the PET substrate 11 on which the carbon electrode part had been formed, and a PET substrate 63 was attached to the PET substrate 11 with the double-sided tapes to construct a flow channel. On an opening 64a formed at one end side (A end) of the flow channel, a reagent-applying reservoir 64 made of a silicone rubber sheet (thickness: 5 mm, SR sheet SR-50; manufactured by Tigers Polymer Corporation) and having a structure shown in FIGS. 31 and 32 was positioned. On another end side (B end), a cellulose pad (CELLULOSE FIBER SAMPLE PADS; manufactured by MILLIPORE), cut to a size of 10 mm×150 mm as an absorbing pad 65, was arranged on the substrate so that it was in immediate contact with the outlet of the flow channel, to construct a capillary flow channel having a carbon electrode part.

5-7. Measurement of HBs Antigen by Electrochemical Analyzer

The constructed capillary flow channel having a carbon electrode part was used to measure an HBs antigen. A mixture prepared by adding 0.83 µL of the ALP-labeled anti-HBs antibody solution (120 µg/mL) to 49.17 µL of an antigen solution (prepared by diluting an HBs antigen with a human serum to a predetermined concentration) was applied to the flow channel from the A end (from the side of the reagent-applying reservoir). Then, 750 μL of the washing solution was added to the reagent-applying reservoir, and transferred in the direction toward the B end by capillarity. Once the whole amount of washing solution had flowed from the reagent reservoir into the flow channel, 500 μL of the substrate solution containing silver ion was added to the reagent reservoir. This solution was transferred in the direction toward the B end by capillarity for 2 minutes, and electrochemical measurements were carried out while maintaining this status.

Each electrochemical measurement was carried out as follows. The connectors for the working, reference, and counter electrodes were connected to an electrochemical analyzer (model 832A; manufactured by ALS). The electric potential was varied between −0.4 V and 0.4 V with respect to the reference electrode (potential increment: 0.005 V, amplitude: 0.05 V, pulse width: 0.1 seconds, and pulse period: 0.2 seconds) to measure the electrochemical response by differential pulse voltammetry (DPV).

Figure 33:
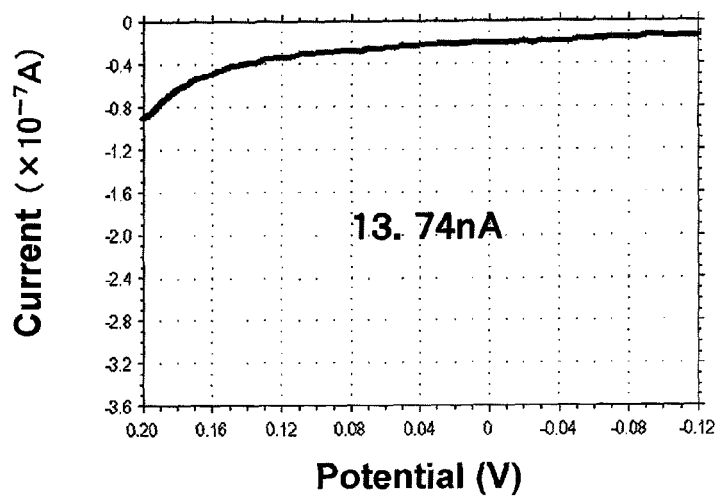
FIG. 33 is a graph showing the result of a DPV measurement of HBs antigen (concentration of antigen=0 U/mL), using the capillary flow channel having a carbon electrode part.
Figure 34:
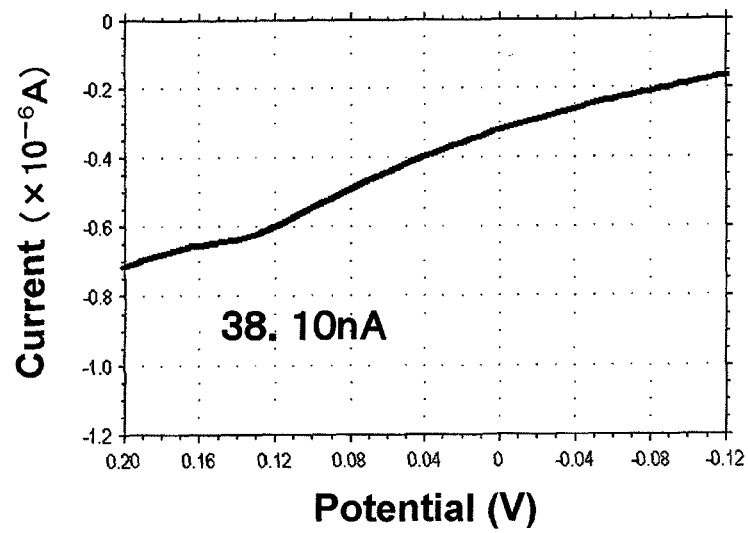
FIG. 34 is a graph showing the result of a DPV measurement of HBs antigen (concentration of antigen=0.25 U/mL), using the capillary flow channel having a carbon electrode part.
Figure 35:
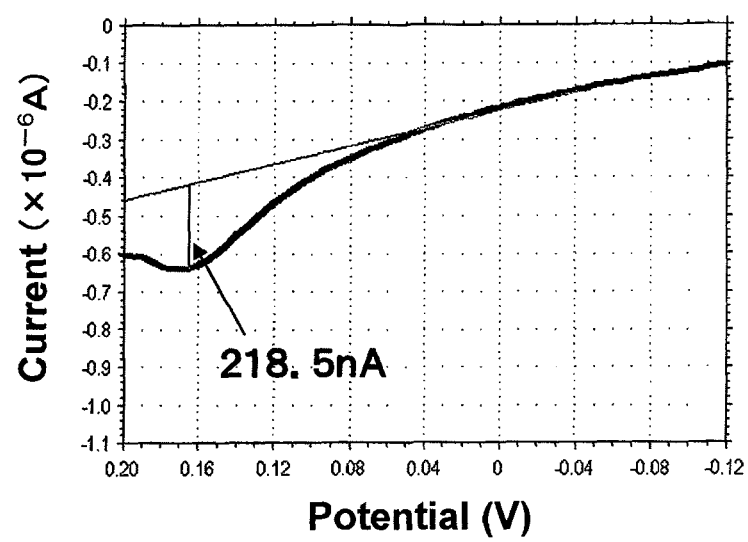
FIG. 35 is a graph showing the result of a DPV measurement of HBs antigen (concentration of antigen=2.5 U/mL), using the capillary flow channel having a carbon electrode part.
Figure 36:
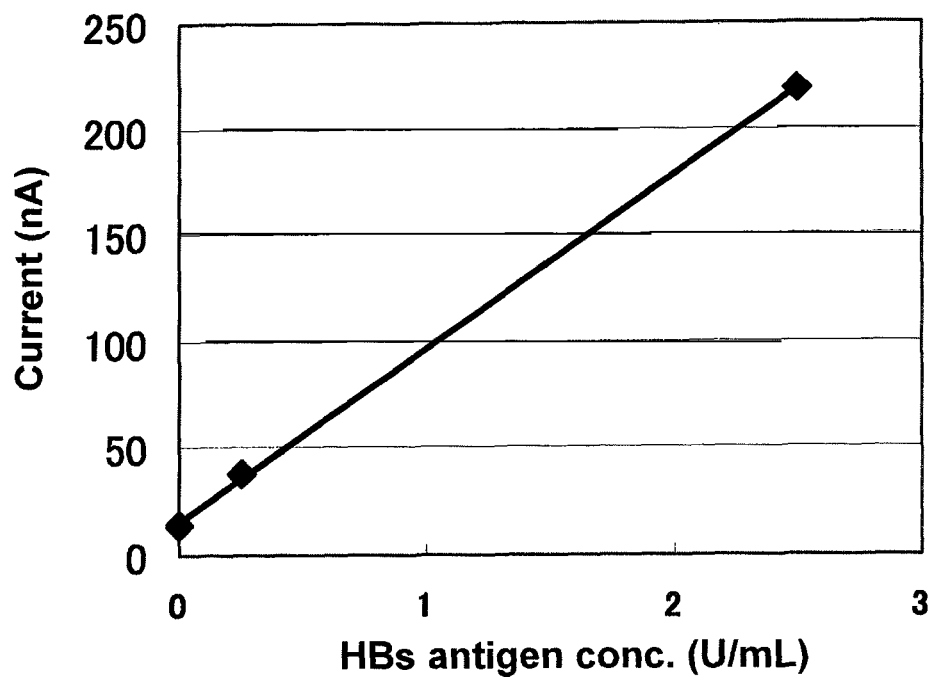
FIG. 36 is a graph showing oxidation current values at an electric potential of +0.165 V obtained in DPV measurements of various concentrations of HBs antigen (concentrations of antigen=0, 0.25, and 2.5 U/mL).
Figure 37:
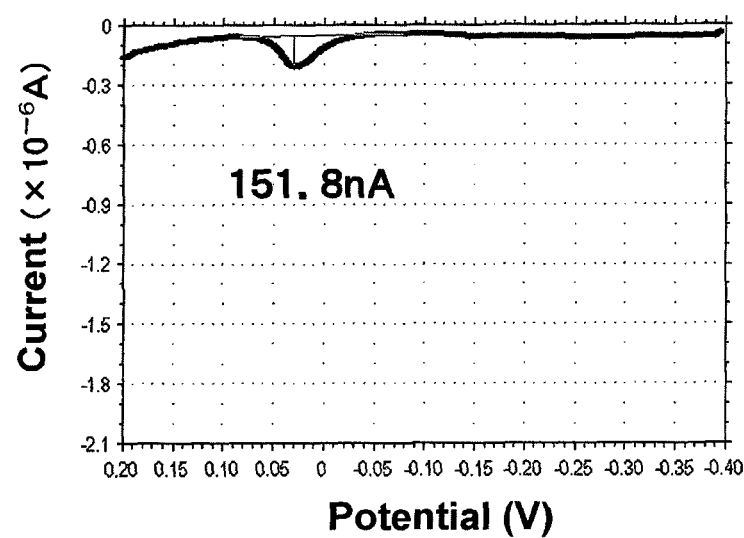
FIG. 37 is a graph showing the result of a DPV measurement of HBs antigen (concentration of antigen=0 U/mL), using a carbon electrode part at a NaCl concentration of 0 mmol/L.
Figure 38:
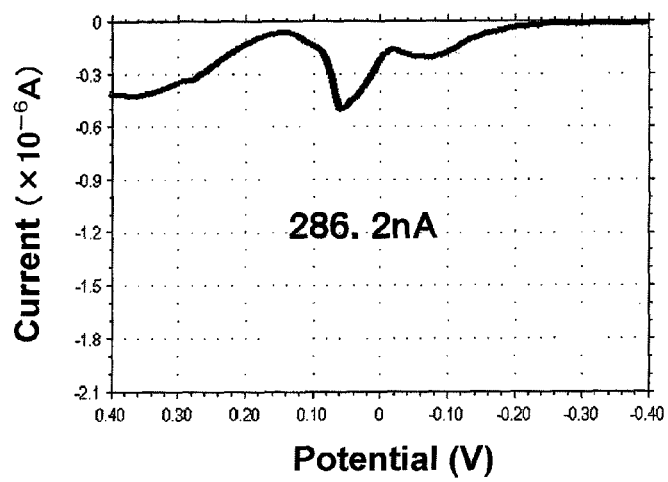
FIG. 38 is a graph showing the result of a DPV measurement of HBs antigen (concentration of antigen=0 U/mL), using a carbon electrode part at a NaCl concentration of 0.5 mmol/L.
Figure 39:
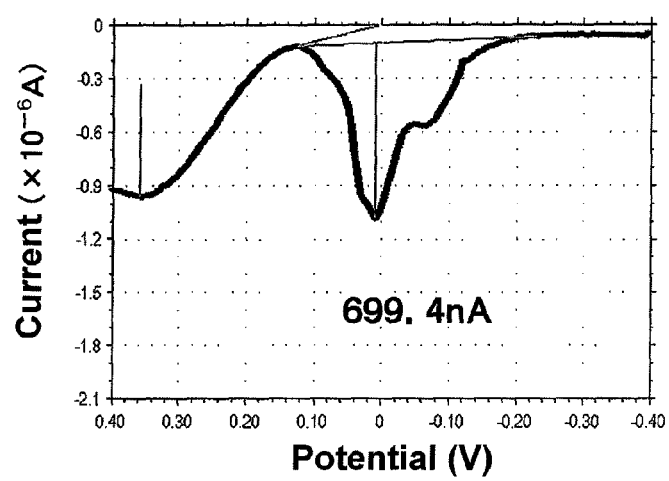
FIG. 39 is a graph showing the result of a DPV measurement of HBs antigen (concentration of antigen=0 U/mL), using a carbon electrode part at a NaCl concentration of 1 mmol/L.
Figure 40:
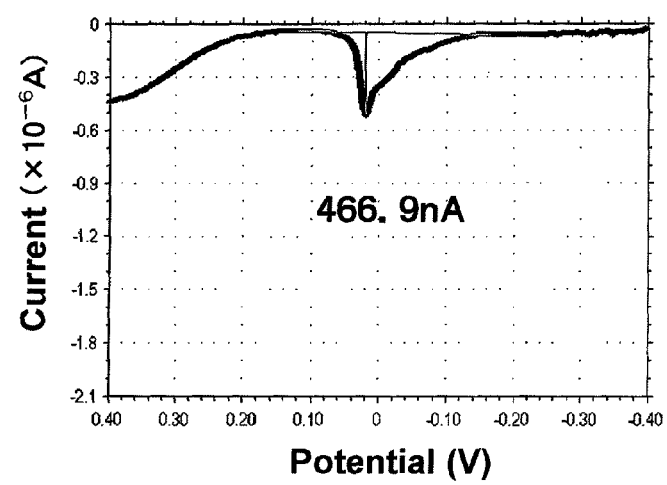
FIG. 40 is a graph showing the result of a DPV measurement of HBs antigen (concentration of antigen=0 U/mL), using a carbon electrode part at a NaCl concentration of 2 mmol/L.
Figure 41:
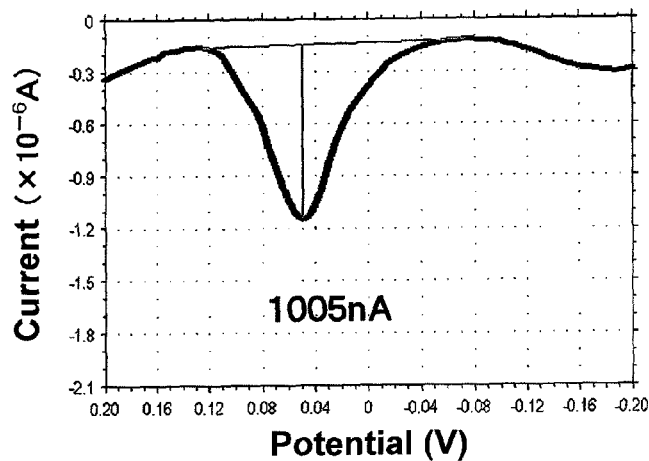
FIG. 41 is a graph showing the result of a DPV measurement of HBs antigen (concentration of antigen=45 U/mL), using a carbon electrode part at a NaCl concentration of 0 mmol/L.
Figure 42:
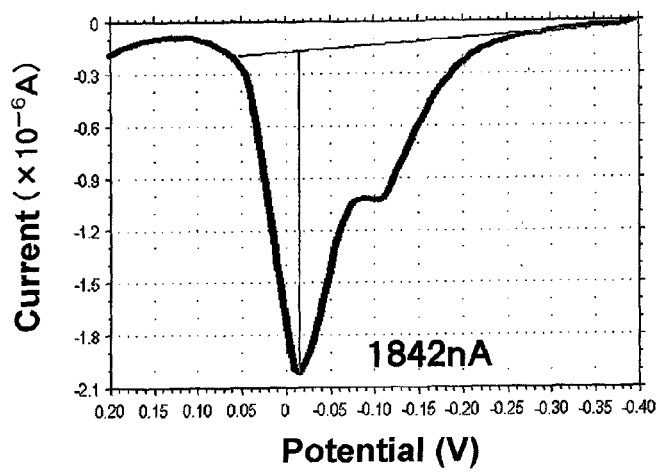
FIG. 42 is a graph showing the result of a DPV measurement of HBs antigen (concentration of antigen=45 U/mL), using a carbon electrode part at a NaCl concentration of 0.5 mmol/L.
Figure 43:
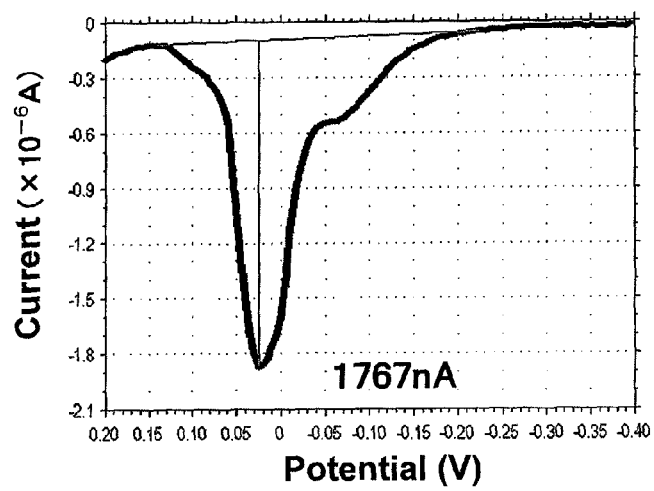
FIG. 43 is a graph showing the result of a DPV measurement of HBs antigen (concentration of antigen=45 U/mL), using a carbon electrode part at a NaCl concentration of 1 mmol/L.
Figure 44:
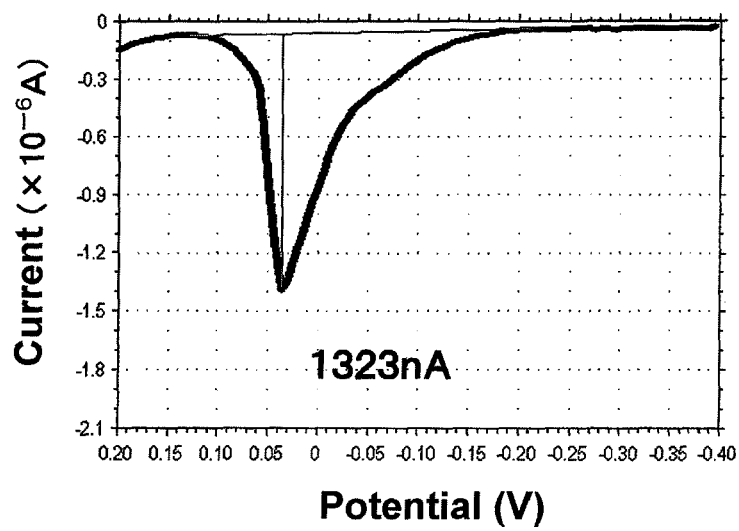
FIG. 44 is a graph showing the result of a DPV measurement of HBs antigen (concentration of antigen=45 U/mL), using a carbon electrode part at a NaCl concentration of 2 mmol/L.

5-8. Results of Measurements (1) Detection of Oxidation Current Caused by the Presence of HBs Antigen The results of DPV measurements where the concentration of HBs antigen was 0, 0.25, and 2.5 U/mL are shown in FIGS. 33 to 35, respectively. At an electric potential of +0.165 V with respect to the reference electrode, the oxidation currents were 13.74 nA, 38.10 nA, and 218.5 nA when the concentrations of HBs antigen were 0, 0.25, and 2.5 U/mL, respectively. As apparent from the graph of FIG. 36, the oxidation current increased dependent on the concentration of HBs antigen, and thus, it was confirmed that the HBs antigen could be quantitatively measured by this method.

Example 6

Measurement of Hepatitis B Surface Antigen (HBsAg) (Effect of Adding NaCl)

6-1. Construction of Electrode Part and Sensing Part

An electrode part was constructed in accordance with the procedure described in item 5-1 of Example 5. The working electrode contained in the electrode part functions as a sensing part.

6-2. Construction of Interaction Reaction Part and Insolubilization Part

An interaction reaction part and an insolubilization part were constructed on the working electrode in accordance with the procedure described in item 1-2 of Example 1.

6-3. Preparation of Solution Containing Anti-HBs Rabbit Polyclonal Antibody (Fab') Labeled with Alkaline Phosphatase (ALP)

A reagent solution was prepared in accordance with the procedure described in item 1-3 of Example 1.

6-4. Preparation of Substrate Solution Containing Silver Ion

As substrate solutions containing silver ion, solutions containing 2 mmol/L p-aminophenylphosphate (pAPP; manufactured by Universal sensors), 0.125 mmol/L $AgNO_3$, 1 mmol/L $MgSO_4$, 0.04 mol/L diethanolamine, and predetermined concentrations (0, 0.5, 1, 2 mmol/L) of NaCl (pH 9.4) were prepared.

6-5. Preparation of Washing Solution

A washing solution was prepared in accordance with the procedure described in item 5-5 of Example 5.

6-6. Construction of Capillary Flow Channel Having Carbon Electrode Part

A capillary flow channel having a carbon electrode part was constructed in accordance with the procedure described in item 5-6 of Example 5.

6-7. Measurement of HBs Antigen by Electrochemical Analyzer

The constructed capillary flow channel having a carbon electrode part was used to measure an HBs antigen. A mixture prepared by adding 0.83 μL of the ALP-labeled anti-HBs antibody solution (120 μg/mL) to 49.17 μL of an antigen solution (prepared by diluting an HBs antigen with a 0.1 mol/L phosphate buffer containing 0.1% BSA to a predetermined concentration) was applied to the flow channel from the A end (from the side of the reagent-applying reservoir). Then, 750 μL of the washing solution was added to the reagent-applying reservoir, and transferred in the direction toward the B end by capillarity. Once the whole amount of washing solution had flowed from the reagent reservoir into the flow channel, 500 μL of the substrate solution containing silver ion was added to the reagent reservoir. This solution was transferred in the direction toward the B end by capillarity for 2 minutes, and electrochemical measurements were carried out while maintaining this status. Each electrochemical measurement was carried out in accordance with the procedure and the conditions described in item 5-7 of Example 5.

6-8. Results of Measurements

The results of DPV measurements where the concentration of HBs antigen was 0 U/mL are shown in FIGS. 37 to 40. The results of DPV measurements where the concentration of HBs antigen was 45 U/mL are shown in FIGS. 41 to 44.

When the concentration of HBs antigen was 45 U/mL and the concentrations of NaCl were 0 mmol/L (FIG. 41), 0.5 mmol/L (FIG. 42), 1 mmol/L (FIG. 43), and 2 mmol/L (FIG. 44), among the oxidation currents at electric potentials of +0.05 0V, −0.015 V, +0.036 V, and +0.026 V with respect to the reference electrode, respectively, the oxidation current at a concentration of 0.5 mmol/L was the highest (1842 nA). When the concentration of HBs antigen was 0 U/mL and the concentrations of NaCl were 0 mmol/L (FIG. 37), 0.5 mmol/L (FIG. 38), 1 mmol/L (FIG. 39), and 2 mmol/L (FIG. 40), the oxidation currents at electric potentials of +0.030 V, +0.055 V, +0.010 V, and +0.020 V with respect to the reference electrode were 151.8 nA, 286.2 nA, 699.4 nA, and 466.9 nA, respectively. It was found that the reactivity could be improved by adding an appropriate amount of NaCl.

Example 7

Confirmation of Effect of Change in Shape of Electrode Surface [Measurement of Hepatitis B Surface Antigen (HBsAg)]

7-1. Construction of Electrode Part and Sensing Part

Figure 45:
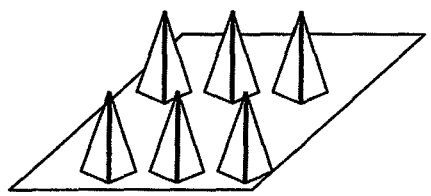
FIG. 45 is a plan view schematically showing the electrode part constructed in Example 7.
Figure 46:
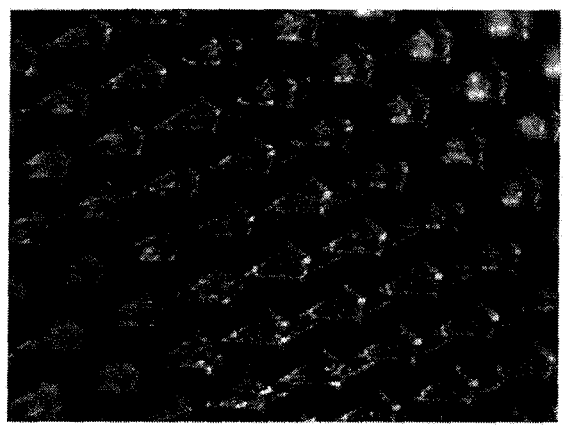
FIG. 46 is an optical micrograph of the electrode part shown in FIG. 45.
Figure 47:
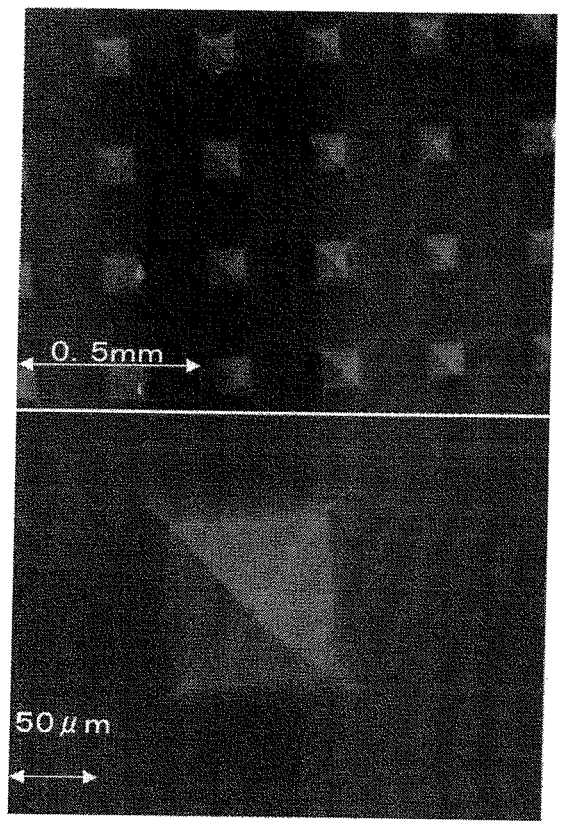
FIG. 47 is an electron micrograph of the electrode part shown in FIG. 45.

An electrode part on which a large number of three-dimensional structures having a pyramid shape as shown in FIGS. 45 to 47 were formed was constructed on a polylactic acid substrate (hereinafter referred to as three-dimensional-structure substrate), and an electrode part and a sensing part were constructed on the three-dimensional-structure substrate, using a mask pattern as shown in FIG. 3, by a sputtering method and a lift-off method. The three-dimensional structures having a pyramid shape and the three-dimensional-structure substrate were constructed by electroforming. From the micrographs shown in FIGS. 46 and 47, the three-dimensional structures having a square base of 135 μm×135 μm and a height of 300 μm were regularly arranged at a density of 12.3 pyramids/mm².

The procedure for constructing the above-mentioned electrode part and the sensing part will be briefly explained. A gold thin film having a thickness of 50 nm was formed on the three-dimensional-structure substrate, and a silver/silver chloride ink (manufactured by BAS Inc.) was applied on a part of the gold thin film to construct a reference electrode 16. To divide the area between the electrode part 12 and a lead part 13, a part of the lead part was covered with an insulating layer 17 to construct the electrode part having a working electrode 14, a counter electrode 15, and the reference electrode 16. The ends opposite to the working electrode, the counter electrode, and the reference electrode function as connectors 18. The working electrode contained in the electrode part functions as a sensing part (hereinafter sometimes referred to as three-dimensionalized electrode part).

7-2. Construction of Interaction Reaction Part and Insolubilization Part

An interaction reaction part and an insolubilization part were constructed on the working electrode in accordance with the procedure described in item 1-2 of Example 1.

7-3. Preparation of Solution Containing Anti-HBs Rabbit Polyclonal Antibody (Fab') Labeled with Alkaline Phosphatase (ALP)

A reagent solution was prepared in accordance with the procedure described in item 1-3 of Example 1.

7-4. Preparation of Substrate Solution Containing Silver Ion

As a substrate solution containing silver ion, a 0.04 mol/L diethanolamine solution (pH 9.4) containing 2 mmol/L p-aminophenylphosphate (pAPP; manufactured by Universal sensors), 0.0625 mmol/L $AgNO_3$, and 1 mmol/L $MgSO_4$ was prepared.

7-5. Construction of Flow Channel and Apparatus for Controlling Flow Conditions

A flow channel and an apparatus for controlling flow conditions were constructed in accordance with the procedure described in item 1-6 of Example 1.

7-6. Measurement of HBs Antigen Using Three-Dimensionalized Electrode Part by Electrochemical Analyzer In accordance with the procedure described in item 1-7 of Example 1, an HBs antigen was measured using the three-dimensionalized electrode part constructed above. As a control for comparison, the electrode part without the three-dimensional structures (hereinafter sometimes referred to as plane electrode part), constructed in Example 1, was used. In this regard, each electrochemical measurement was carried out in accordance with the procedure and the conditions described in item 5-7 of Example 5.

7-7. Results of Measurements (1) Detection of Oxidation Current Caused by the Presence of HBs Antigen (Compound to be Measured)

Figure 48:
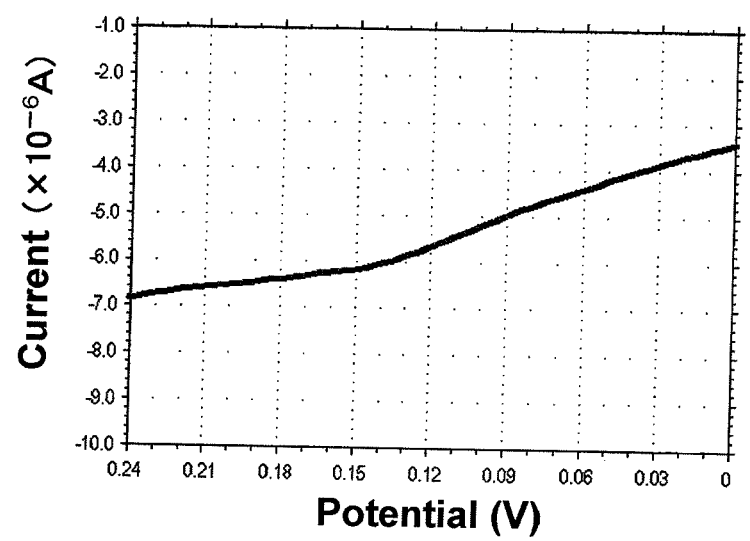
FIG. 48 is a graph showing the result of a DPV measurement of HBs antigen (concentration of antigen=0 U/mL), using the three-dimensionalized electrode part.
Figure 49:
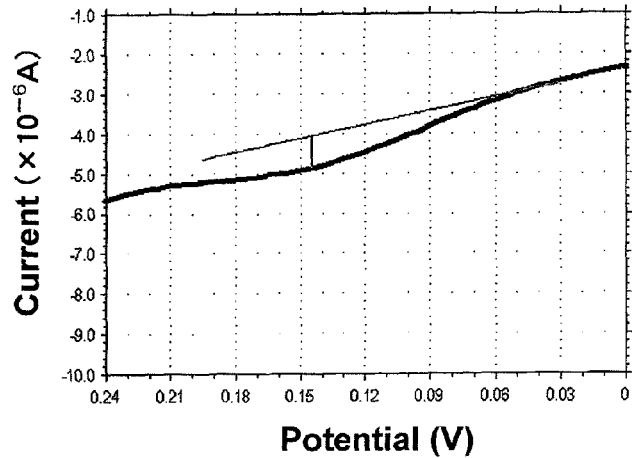
FIG. 49 is a graph showing the result of a DPV measurement of HBs antigen (concentration of antigen=0.7 U/mL), using the three-dimensionalized electrode part.
Figure 50:
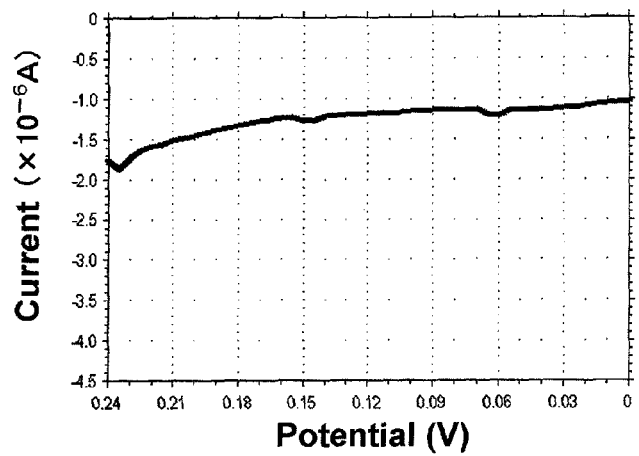
FIG. 50 is a graph showing the result of a DPV measurement of HBs antigen (concentration of antigen=0 U/mL), using the plane electrode part.
Figure 51:
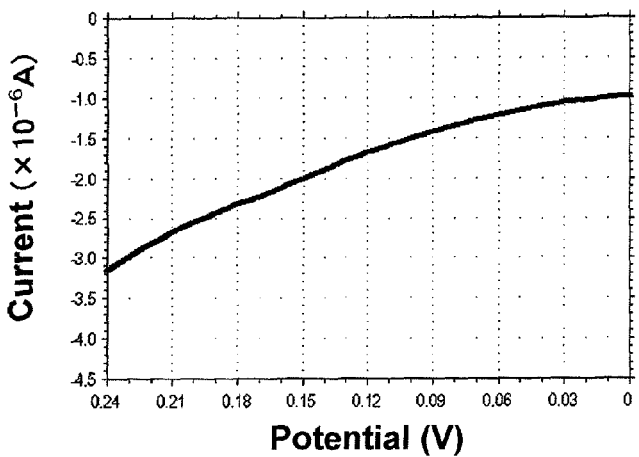
FIG. 51 is a graph showing the result of a DPV measurement of HBs antigen (concentration of antigen=0.7 U/mL), using the plane electrode part.

The result of a DPV measurement where the three-dimensionalized electrode part was used and the concentration of HBs antigen was 0 U/mL is shown in FIG. 48, and the result of a DPV measurement where the concentration of HBs antigen was 0.7 U/mL is shown in FIG. 49. As a control, the result of a DPV measurement where the electrode part without the three-dimensional structures (plane electrode part) was used and the concentration of HBs antigen was 0 U/mL is shown in FIG. 50, and the result of a DPV measurement where the concentration of HBs antigen was 0.7 U/mL is shown in FIG. 51. In these measurements, the feed of liquid to the flow channel (i.e., flow conditions) was carried out at a flow rate of 360 μL/min through the whole process (from the feed of buffer A for 2 minutes to the electrochemical measurement).

When the concentration of HBs antigen was 0.7 U/mL (FIG. 49), as an oxidation current accompanied by an oxidation reaction of deposited silver, an oxidation current of 800.7 nA was detected at an electric potential of +0.145 V (oxidation potential) with respect to the reference electrode. When the concentration of HBs antigen was 0 U/mL (FIG. 48), the oxidation current was 343 nA. With respect to the plane electrode part, although an oxidation current was observed in Example 1 when the concentration of HBs antigen was 48 U/mL, no oxidation currents similar to those observed in the measurements using the three-dimensionalized electrode part were detected in both cases [0 U/mL (FIG. 50) and 0.7 U/mL (FIG. 51)]. It was found from these results that the detection sensitivity of HBs antigen could be significantly improved by the three-dimensionalization of the electrode part.

INDUSTRIAL APPLICABILITY

The present invention is applicable to high sensitivity analysis, for example, clinical tests, diagnosis, food analysis, and environmental analysis.

Although the present invention has been described with reference to specific embodiments, various changes and modifications obvious to those skilled in the art are possible without departing from the scope of the appended claims.

The invention claimed is:

1. An analysis method characterized by comprising the steps of:
   (a) reacting a substance to be analyzed with at least a specific partner which exhibits a selective interaction with the substance, converting a soluble substance to an insoluble substance by an insolubilization reaction, in correlation with the amount of the substance to be analyzed contained in a sample, and depositing the insoluble substance on a sensing part, and
   (b) electrically analyzing the insoluble substance deposited on the sensing part, wherein the deposition of the insoluble substance in step (a) is carried out under flow conditions.

2. The method according to claim 1, wherein the specific partner is an enzyme.

3. The method according to claim 1, wherein step (a) comprises:
   (1) forming a complex comprising a substance to be analyzed, a specific partner which exhibits a selective interaction with the substance, and a labeling substance, in correlation with the amount of the substance to be analyzed contained in a sample, and
   (2) converting a soluble substance to an insoluble substance by an insolubilization reaction directly or indirectly caused by the labeling substance contained in the formed complex, and depositing the insoluble substance on a sensing part, wherein the deposition of the insoluble substance in step (2) is carried out under flow conditions.

4. The method according to claim 3, wherein the labeling substance is a hydrolase.

5. The method according to claim 4, wherein the hydrolase is alkaline phosphatase.

6. The method according to claim 1, wherein the insolubilization reaction is an oxidation-reduction reaction.

7. The method according to claim 1, wherein the soluble substance is selected from an inorganic ion, an organic ion, an enzyme substrate or its reaction product, and a dye.

8. The method according to claim 7, wherein the soluble substance is a metal ion.

9. The method according to claim 8, wherein the metal ion is a silver ion.

10. The method according to claim 1, wherein the sensing part is composed of any one of a metal, a polymer, carbon, a nanotube structure, graphite, or inorganic substance, or a combination thereof.

11. The method according to claim 1, wherein the sensing part has one or more three-dimensional structures having an acute-angle-like shape.

12. The method according to claim 1, wherein the specific partner is immobilized on the sensing part.

13. The method according to claim 1, wherein the flow conditions are an enforced flow or a spontaneous flow.

14. The method according to 1, wherein the analysis method comprising the electric analysis step is an amperometric analysis.

* * * * *